US009765385B2

(12) United States Patent
Rounseville et al.

(10) Patent No.: US 9,765,385 B2
(45) Date of Patent: Sep. 19, 2017

(54) NUCLEASE PROTECTION METHODS FOR DETECTION OF NUCLEOTIDE VARIANTS

(71) Applicant: HTG Molecular Diagnostics, Inc., Tuscon, AZ (US)

(72) Inventors: Matt Rounseville, Tuscon, AZ (US); Bruce Seligmann, Tucson, AZ (US)

(73) Assignee: HTG Molecular Diagnostics, Inc., Tucson, AZ (US)

( * ) Notice: Subject to any disclaimer, the term of this patent is extended or adjusted under 35 U.S.C. 154(b) by 101 days.

(21) Appl. No.: 14/411,806

(22) PCT Filed: Jun. 28, 2013

(86) PCT No.: PCT/US2013/048610
§ 371 (c)(1),
(2) Date: Dec. 29, 2014

(87) PCT Pub. No.: WO2014/005038
PCT Pub. Date: Jan. 3, 2014

(65) Prior Publication Data
US 2015/0191770 A1 Jul. 9, 2015

Related U.S. Application Data

(60) Provisional application No. 61/829,102, filed on May 30, 2013, provisional application No. 61/666,456, filed on Jun. 29, 2012.

(51) Int. Cl.
C12Q 1/68 (2006.01)

(52) U.S. Cl.
CPC ........... *C12Q 1/683* (2013.01); *C12Q 1/6827* (2013.01); *C12Q 2521/325* (2013.01); *C12Q 2561/108* (2013.01)

(58) Field of Classification Search
None
See application file for complete search history.

(56) References Cited

U.S. PATENT DOCUMENTS 6,043,031 A 3/2000 Köster et al.
7,659,063 B2 2/2010 Kris et al.
(Continued)

FOREIGN PATENT DOCUMENTS

JP 2011-135884 7/2011
WO WO 96/36731 11/1996
(Continued)

OTHER PUBLICATIONS

Pikkard et al., "Detecting Differential Expression of Parental or Progenitor Alleles in Genetic Hybrids and Allopolyploids," *Methods in Enzymology*, vol. 395, pp. 554-569, 2005.
(Continued)

*Primary Examiner* — Joseph G Dauner
(74) *Attorney, Agent, or Firm* — Klarquist Sparkman, LLP

(57) ABSTRACT

Disclosed herein are methods for detecting presence of a nucleotide variant in a target nucleic acid utilizing a nuclease protection assay. The methods include contacting a sample with at least two probes, wherein the first probe is complementary to the wild-type (non-variant) nucleotide(s) at the nucleotide variant position(s) in the target nucleic acid and the second probe is complementary to the variant nucleotide(s) at the nucleotide variant position(s) in the target nucleic acid, under conditions sufficient for the probes to hybridize to the target nucleic acid, producing a mixture of hybridized and unhybridized nucleic acids. The mixture is contacted with a nuclease specific for single-stranded nucleic acid molecules under conditions sufficient to remove unhybridized nucleic acid molecules (or unhybridized portions of nucleic acid molecules). The presence of the at least
(Continued)

two probes is then detected, thereby detecting the presence of the variant and/or non-variant target nucleic acid in the sample.

20 Claims, 10 Drawing Sheets

(56) References Cited

U.S. PATENT DOCUMENTS

| | | | |
|---|---|---|---|
| 2003/0138838 A1* | 7/2003 | Wang | C12Q 1/6837 435/6.12 |
| 2005/0042638 A1 | 2/2005 | Arnold et al. | |
| 2005/0164204 A1* | 7/2005 | Reed | C12Q 1/6806 435/6.1 |
| 2008/0076121 A1 | 3/2008 | Wolber | |
| 2009/0197775 A1 | 8/2009 | Bachmann et al. | |
| 2010/0105572 A1 | 4/2010 | Kris et al. | |
| 2010/0323914 A1 | 12/2010 | Fu | |

FOREIGN PATENT DOCUMENTS

| | | |
|---|---|---|
| WO | WO 99/32663 | 7/1999 |
| WO | WO 00/56926 | 9/2000 |
| WO | WO 02/16647 | 2/2002 |
| WO | WO 2006/042303 | 4/2006 |
| WO | WO 2008/121927 | 10/2008 |
| WO | WO 2011/056863 | 5/2011 |

OTHER PUBLICATIONS

Rounseville et al., "Development of an automated RNA-based nuclease protection assay for the detection of expressed EML-ALL fusions, EGFR, and KRAS mutations in NSCLC," *2013 ASCO Annual Meeting*, Abstract No. e22185, May 31-Jun. 4, 2013 (2 pages).

Mun et al., "SNPs detection by a single-strand specific nuclease on a PNA zip-code microarray," *Biosensors and Bioelectronics*, vol. 24, No. 6, pp. 1706-1711, 2009.

* cited by examiner

FIG. 1A
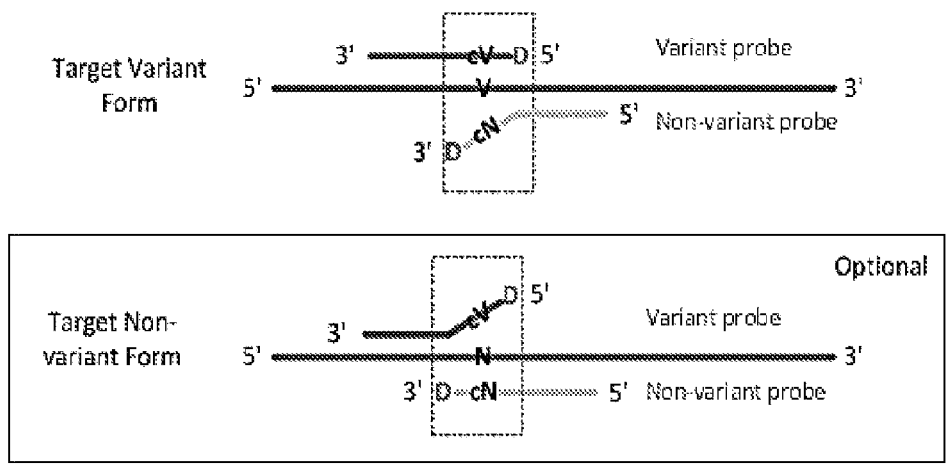
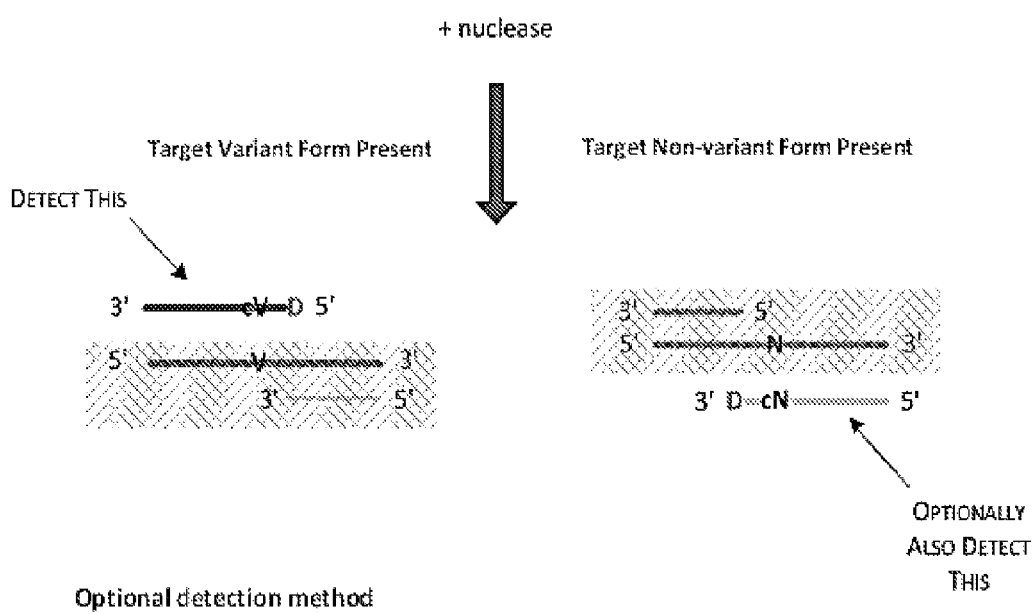
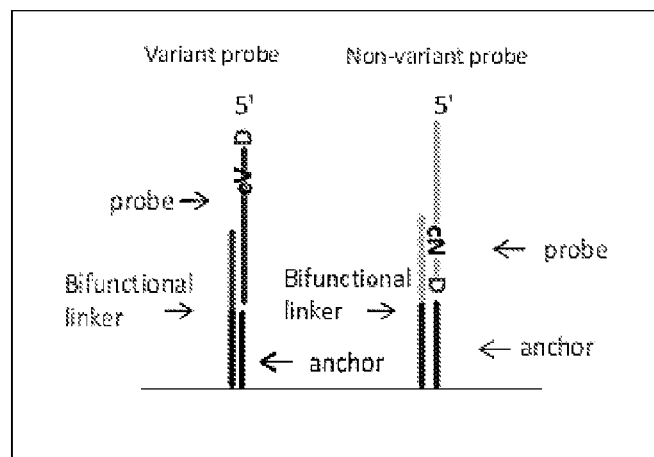

FIG. 2

```
Target RNA:              ACCTCCACCGTGCAGCTCATGCCCTTCGGCT    (SEQ ID NO: 11)  wt-Probe
SNP-Probe:             B-GTGCGTCGAGTACGGGAAGCCGA            (SEQ ID NO: 12)
                        TGGAGGTGGCACGTCGAGTAGTACG-B         (SEQ ID NO: 13)

Target RNA:              ACCTCCACCGTGCAGCTCATCAGCAGCTCATGCCCTTCGGCT  (SEQ ID NO: 11)  wt-Probe
SNP-Probe:             B-GTGCGTCGAGTACGGGAAGCCGA            (SEQ ID NO: 14)
                        TGGAGGTGGCACGTCGAGTAGTACG-B         (SEQ ID NO: 13)
```

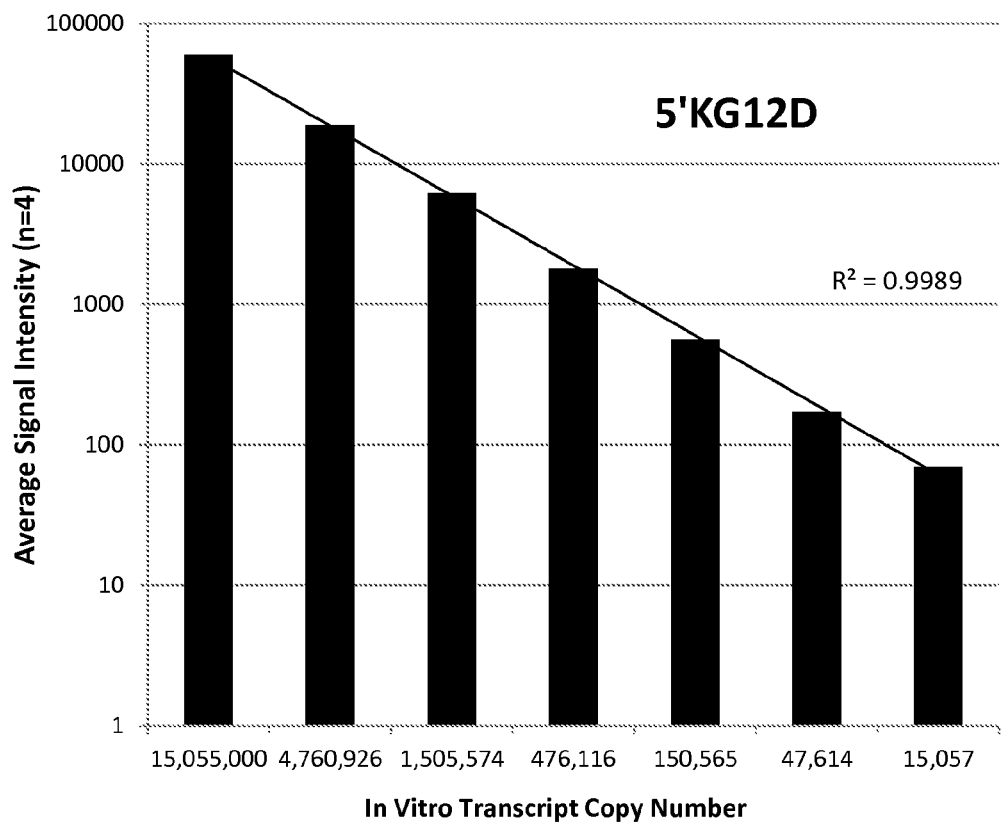

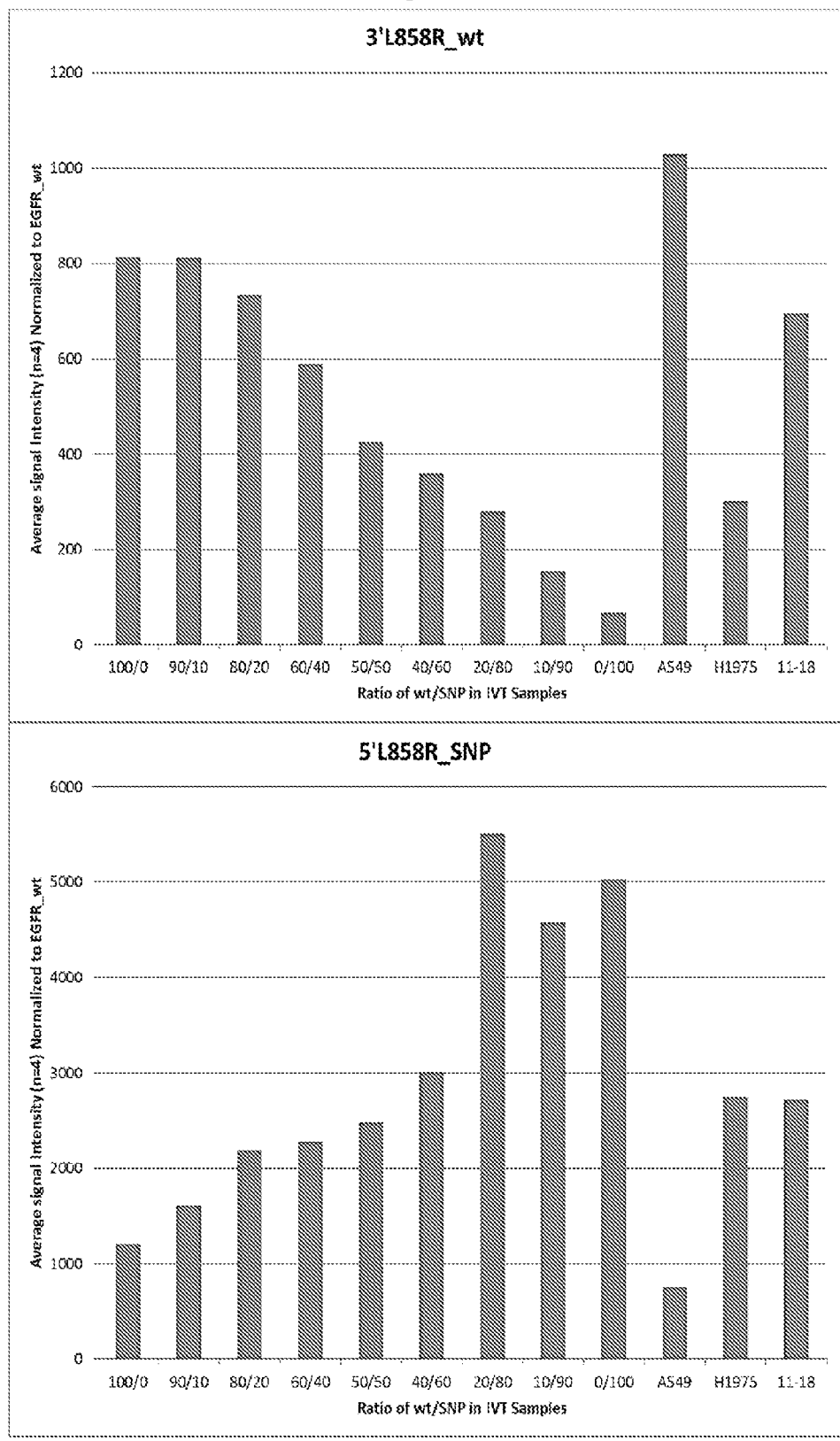

NUCLEASE PROTECTION METHODS FOR DETECTION OF NUCLEOTIDE VARIANTS

CROSS REFERENCE TO RELATED APPLICATIONS

This is the §371 U.S. National Stage of International Application No. PCT/US2013/048610, filed Jun. 28, 2013, which was published in English under PCT Article 21(2), which in turn claims the benefit of U.S. Provisional Application No. 61/666,456, filed Jun. 29, 2012, and U.S. Provisional Application No. 61/829,102, filed May 30, 2013, both of which are incorporated herein by reference in their entirety.

FIELD

This disclosure relates to methods for detecting one or more nucleotide variants in a target nucleic acid molecule, particularly utilizing nuclease protection methods.

BACKGROUND

Many diseases or disorders are characterized by disruptions in protein expression or activity, or in cellular signaling pathways that lead to aberrant control of cellular processes or to uncontrolled growth and proliferation of cells. These disruptions are often caused by genetic changes (also called mutations) or other changes that affect the activity or expression of particular proteins. Diagnosis and/or selection of treatment for many disorders include identification of particular genetic changes in a sample from a subject known or suspected of having a particular disorder.

There is a need for continued development of diagnostic tests and methods to detect mutations and molecular signatures implicated in the onset and progression of human disease. Such methods and diagnostic tests will, among other things, facilitate the screening of new drugs, as well as development of methods to select patients for therapy and monitor the responsiveness of patients to targeted therapy.

SUMMARY

Disclosed herein are methods for detecting the presence of a nucleotide variant in a target nucleic acid utilizing a nuclease protection assay. In one example, the methods include contacting a sample with at least two probes, wherein the first probe includes nucleotide(s) complementary to the wild-type (non-variant) nucleotide(s) at the nucleotide variant position(s) in the target nucleic acid and the second probe includes nucleotide(s) complementary to the variant nucleotide(s) at the nucleotide variant position(s) in the target nucleic acid. The sample is contacted with the at least two probes under conditions sufficient for the probes to hybridize to the target nucleic acid, producing a mixture of hybridized and unhybridized nucleic acid molecules. The mixture is contacted with a nuclease specific for single-stranded nucleic acid molecules under conditions sufficient to remove unhybridized nucleic acid molecules (or unhybridized portions of nucleic acid molecules). The presence and/or amount of the at least two probes remaining following nuclease treatment is then detected, thereby detecting the presence of the variant and/or non-variant target nucleic acid in the sample.

The foregoing and other features of the disclosure will become more apparent from the following detailed description, which proceeds with reference to the accompanying figures.

BRIEF DESCRIPTION OF THE DRAWINGS

FIG. 1A is a schematic showing an exemplary nuclease protection assay for detecting the presence of a non-variant (wild type) or variant target nucleic acid in a sample. In this exemplary method, the variant position is located near the end of each of the probes (for example, about 2-8 bases from the end) and the probe sequences only overlap in the region of the variant position (referred to herein in some examples as "offset" or "competimer" probes). The non-variant probe includes a nucleotide (cN) complementary to the non-variant (wild type) nucleotide (N) at the variant position, which is near the 3'-end of the probe and which includes a detectable label (D) at the 3'-end of the probe. The variant probe includes a nucleotide (cV) complementary to the variant nucleotide (V) at the variant position, which is near the 5'-end of the probe and which includes a detectable label (D) at the 5'-end of the probe. The two probes compete for hybridization to the target nucleic acid (for example, the target variant form and/or the target non-variant form, if present) and probe hybridization is mutually exclusive at the overlapping region (which includes the detectable label). If the target variant form is present in the sample, the variant probe will hybridize, will be protected from nuclease digestion, and the label will be detected, while the 3' portion of the non-variant probe will not hybridize and the mismatch portion, including the label, will be cleaved by the nuclease and will not be subsequently detected. If the target non-variant form is present in the sample, the non-variant probe will hybridize, will be protected from nuclease digestion, and the label will be detected, while the 5' portion of the variant probe will not hybridize and the mismatch portion, including the detectable label, will be cleaved by the nuclease and will not be subsequently detected. If both the target variant and non-variant forms are present in the sample, both of the probes will be protected at a ratio similar to the ratio of variant to non-variant target forms present in the sample, and both will be detected. The box at the bottom shows an exemplary detection method utilizing a microarray with distinct anchors attached to a surface. Each anchor binds a programmable bifunctional linker having a portion complementary to the anchor and a portion complementary to the variant probe (left) or a portion complementary to the non-variant probe (right). Following nuclease treatment, the probes are hybridized to the array and the label is detected.

FIG. 2 is a schematic showing exemplary non-variant and variant "offset" ("competimer") probes for epidermal growth factor receptor (EGFR) where the variant position is three bases from the end of each of the probes. The non-variant probe (wt probe; SEQ ID NO: 11) will hybridize perfectly to the non-variant target RNA (SEQ ID NO: 12) and be protected from nuclease cleavage, while the variant probe (SNP probe; SEQ ID NO: 13) will not hybridize perfectly at the end due to the mismatch and will be susceptible to nuclease cleavage (top panel). The variant probe (SNP-probe) will hybridize perfectly to the variant target RNA (SEQ ID NO: 14) and be protected from nuclease cleavage, while the non-variant probe (wt-probe) will not hybridize perfectly at the end due to the mismatch and will be susceptible to nuclease cleavage (bottom panel).

FIG. 3 is a graph showing average signal intensity at varying in vitro transcript (IVT) copy numbers for the KRAS G12D variant probe (SEQ ID NO: 10), demonstrating linearity and sensitivity of the assay.

FIG. 4B is a pair of graphs showing wild type (top) and variant (bottom) probe signal for EGFR L858R probes in IVT mixtures and the indicated cell lines.

SEQUENCES

Figure 1B:
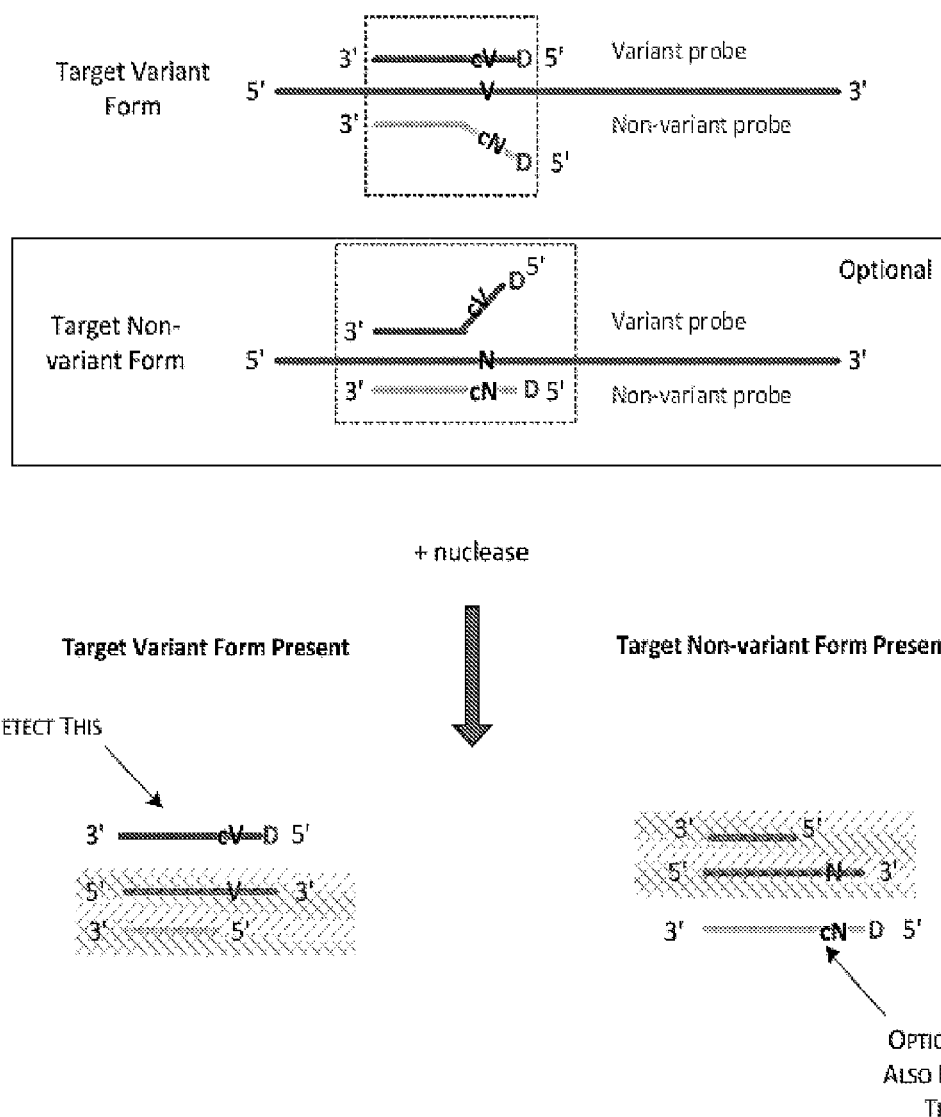
FIG. 1B is a schematic of an additional exemplary nuclease protection assay for detecting the presence of a non-variant (wild type) or variant target nucleic acid in a sample. In this exemplary method, the variant position is located near the end of each of the probes (for example, about 2-8 bases from the end) and the probe sequences are identical except for the variant position(s) ("overlap" probes). The non-variant probe includes a nucleotide (cN) complementary to the non-variant or wild type nucleotide (N) at the variant position, which is near the 5'-end of the probe and which includes a detectable label (D) at the 5'-end of the probe. The variant probe includes a nucleotide (cV) complementary to the variant nucleotide (V) at the variant position, which is near the 5'-end of the probe and which includes a detectable label (D) at the 5'-end of the probe. The two probes compete for hybridization to the target nucleic acid (for example, the target variant form and/or the target non-variant form, if present) and probe hybridization is mutually exclusive. If the target variant form is present in the sample, the variant probe will hybridize, will be protected from nuclease digestion, and the label will be detected, while at least the 5' portion of the non-variant probe will not hybridize and the mismatch portion, including the detectable label, will be cleaved by the nuclease and will not be subsequently detected. If the target non-variant form is present in the sample, the non-variant probe will hybridize, will be protected from nuclease digestion, and the label will be detected, while at least the 5' portion of the variant probe will not hybridize and the mismatch portion, including the detectable label, will be cleaved by the nuclease and will not be subsequently detected. If both the target variant and non-variant forms are present in the sample, both of the probes will be protected at a ratio similar to the ratio of variant to non-variant forms present in the sample, and both will be detected.

The nucleic acid sequences listed herein are shown using standard letter abbreviations for nucleotide bases, as defined in 37 C.F.R. 1.822. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Dec. 17, 2014 and is 3,553 bytes, which is incorporated by reference herein.

SEQ ID NOs: 1 and 2 are exemplary KRAS Q61H wild type and variant probes, respectively.

SEQ ID NOs: 3 and 4 are exemplary EGFR D761Y wild type and variant probes, respectively.

SEQ ID NOs: 5 and 6 are exemplary EGFR T790M wild type and variant probes, respectively.

SEQ ID NOs: 7 and 8 are exemplary EGFR L858R wild type and variant probes, respectively.

SEQ ID NOs: 9 and 10 are exemplary KRAS G12D wild type and variant probes, respectively.

SEQ ID NO: 11 is an exemplary EGFR wild-type (non-variant probe).

SEQ ID NO: 12 is an exemplary EGFR non-variant nucleic acid.

SEQ ID NO: 13 is an exemplary EGFR SNP (variant) probe.

SEQ ID NO: 14 is an exemplary EGFR variant nucleic acid.

SEQ ID NOs: 15 and 16 are exemplary BRAF V600 wild type and V600E variant probes, respectively.

DETAILED DESCRIPTION

Disclosed herein are methods for detecting the presence and/or amount of nucleotide variants in a target nucleic acid utilizing a nuclease protection assay. Nucleotide(s) complementary to wild-type (non-variant) or variant nucleotide(s) are included in the probes utilized in the assay. If the non-variant sequence is present in the sample, the non-variant probe will hybridize perfectly with the target nucleic acid and will be protected from nuclease digestion. If the variant sequence is present in the sample, the non-variant probe will hybridize to the variant target nucleic acid, but will include one or more "mismatches" with the target and will be susceptible to nuclease digestion. Similarly, if the variant sequence is present in the sample, the variant probe will hybridize perfectly with the target nucleic acid and will be protected from nuclease digestion. If the non-variant sequence is present in the sample, the variant probe will hybridize to the non-variant target nucleic acid, but will include one or more "mismatches" with the target and will be susceptible to nuclease digestion.

Without being bound by theory, it is believed that the ends of hybridized probes "breathe," for example, the end bases are hybridized to their matching bases only part of the time due to the on/off kinetics of hybridization. This theoretically makes the end bases of a probe susceptible to nuclease cleavage at least part of the time, even if the probe is perfectly matched to the target nucleic acid. Thus, placement of the variant nucleotide at or near the end of a probe can result in susceptibility to nuclease cleavage even if the probe is a perfect match to the target. In some examples, for example if a probe is short (for example, less than 18 bases), it is believed that a mismatch anywhere along the probe can destabilize the hybrid relative to a perfectly matching probe, such that the probe including the mismatch will be sensitive to nuclease digestion.

In the methods disclosed herein, the variant or non-variant nucleotide position(s) are internal to the probes, that is, they are not at the end of the probes. Without being bound by theory, it is believed that the presence of a mismatch internal to the probe will destabilize the end bases due to "breathing" of hybridized bases at the end of a probe, even though the end bases are perfectly complementary to the target. Surprisingly, it has been found that the degree of destabilization is sufficient for at least S1 nuclease to cleave the matched bases, as well as the mismatched base(s). This destabilization allows placement of the variant nucleotide position(s) at least 2 to 8 bases (for example, 3 to 6 bases) from the end (either the 5'-end or the 3'-end) of the probes for detection of the presence of a variant in a target nucleic acid in a sample. The disclosed methods thus allow detection of the specific sequence of a variant in a sample (not just presence of a difference from wild-type), as well as improved specificity, reliability, and quantification of samples including a mixture of variant and non-variant target nucleic acids.

I. ABBREVIATIONS

BRAF v-Raf murine sarcoma viral oncogene homolog B1
EGFR epidermal growth factor receptor
FFPE formalin-fixed paraffin embedded
IVT in vitro transcript
KRAS V-Ki-ras2 Kirsten rat sarcoma viral oncogene homolog
SNP single nucleotide polymorphism
SNV single nucleotide variant
and as otherwise set forth throughout the specification, claims, and abstract.

II. TERMS

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), The *Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." As used herein, "comprises" means "includes." Thus, "comprising A or B," means "including A, B, or A and B," without excluding additional elements. All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Conditions sufficient for: Any environment that permits the desired activity, for example, that permits specific binding or hybridization between two nucleic acid molecules (such as a probe and a target nucleic acid or between a probe and a bifunctional ("programming") linker) or that permits a nuclease to remove (or digest) unbound nucleic acids.

Contact: Placement in direct physical association; includes both in solid and liquid form.

For example, contacting can occur in vitro with a nucleic acid probe and biological sample in solution.

Detect: To determine if an agent (such as a signal, particular nucleotide, amino acid, nucleic acid molecule, and/or organism) is present or absent. In some examples, this can further include quantification. For example, use of the disclosed methods and probes in particular examples permits detection and/or identification of a nucleotide variant in a target nucleic acid in a sample.

Detectable label: A compound or composition that is conjugated directly or indirectly to another molecule (such as a nucleic acid molecule or a nucleotide) to facilitate detection of that molecule. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes disclosed herein are described below. Methods for labeling nucleic acids, and guidance in the choice of labels useful for various purposes, are discussed, e.g., in Sambrook and Russell, in *Molecular Cloning: A Laboratory Manual*, 3$^{rd}$ Ed., Cold Spring Harbor Laboratory Press (2001) and Ausubel et al., in *Current Protocols in Molecular Biology*, Greene Publishing Associates and Wiley-Intersciences (1987, and including updates).

Hybridization: The ability of complementary single-stranded DNA, RNA, or DNA/RNA hybrids to form a duplex molecule (also referred to as a hybridization complex). Nucleic acid hybridization techniques can be used to form hybridization complexes between a nucleic acid probe, and the nucleic acid it is designed to target.

"Specifically hybridizable" and "specifically complementary" are terms that indicate a sufficient degree of complementarity such that stable and specific binding occurs between the oligonucleotide (or its analog) and the nucleic acid target (such as DNA or RNA target, such as mRNA or miRNA). The oligonucleotide or oligonucleotide analog need not be 100% complementary to its target sequence to be specifically hybridizable. Specific hybridization is also referred to herein as "specific binding."

Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11).

Melting temperature ($T_m$): Also known as $TM_{50}$. The temperature at which half of the nucleic acid molecules in a mixture are double-stranded and half of the nucleic acid molecules are single-stranded. In some examples, for example when referring to an oligonucleotide (such as a probe), the $T_m$ is the temperature at which 50% of the oligonucleotide and its complement are in a duplex. Methods for determining the $T_m$ for DNA or RNA are known to one of ordinary skill in the art.

Nuclease: An enzyme that cleaves a phosphodiester bond. An endonuclease is an enzyme that cleaves an internal phosphodiester bond within a nucleotide chain (in contrast to exonucleases, which cleave a phosphodiester bond at the end of a nucleotide chain). Endonucleases include restriction endonucleases or other site-specific endonucleases (which cleave DNA at sequence specific sites), DNase I, S1 nuclease, Mung bean nuclease, Ribonuclease A, Ribonuclease T1, RNase I, RNase PhyM, RNase U2, RNase CLB, micrococcal nuclease, and apurinic/apyrimidinic endonucleases. Exonucleases include exonuclease III, exonuclease VII, and Bal 31 nuclease. In particular examples, a nuclease is specific for single-stranded nucleic acids, such as S1 nuclease, Mung bean nuclease, Ribonuclease A, or Ribonuclease T1.

Nucleotide variant: A change or alteration in a nucleic acid sequence, such as change in nucleic acid sequence at one or more bases in a target nucleic acid (including substitution, insertion, duplication, and/or deletion of one or more nucleotides). The nucleotide variant can be those variations (DNA sequence differences) which are generally found between individuals or different ethnic groups and geographic locations which, while having a different sequence, produce functionally equivalent gene products. The term can also refer to variants in the sequence which can lead to gene products that are not functionally equivalent. The term nucleotide variant also encompasses variations which can be classified as alleles and/or mutations which can produce gene products which may have an altered function, produce no gene product, an inactive gene product, or an active gene product produced at an abnormal rate or in an inappropriate tissue or in response to an inappropriate stimulus. In some non-limiting examples, a nucleotide variant is a single nucleotide variant (SNV) or single nucleotide polymorphism (SNP).

Nucleotide variants can be referred to, for instance, by the nucleotide position(s) at which the variation exists (e.g., "nucleotide variant position(s)"), by the change in nucleic acid or amino acid sequence caused by the nucleotide variation, or by a change in some other characteristic of the nucleic acid molecule or protein that is linked to the variation.

Probe: A nucleic acid molecule capable of hybridizing with a target nucleic acid molecule (e.g., a target DNA or RNA (such as mRNA) nucleic acid molecule) and is capable of being detected either directly or indirectly. Thus probes permit the detection, and in some examples quantification, of a target nucleic acid molecule, such as an mRNA. In some examples, a probe includes a detectable label.

Sample: A biological specimen containing DNA (for example, genomic DNA or cDNA), RNA (including mRNA or miRNA), protein, or combinations thereof, obtained from a subject. Examples include, but are not limited to cells, cell lysates, chromosomal preparations, peripheral blood, urine, saliva, tissue biopsy (such as a tumor biopsy or lymph node biopsy), fine needle aspirate, surgical specimen, bone marrow, amniocentesis samples, and autopsy material. In one example, a sample includes RNA, such as mRNA. In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples).

Subject: Any multi-cellular vertebrate organism, such as human and non-human mammals (e.g., veterinary subjects).

Surface (or substrate): Any solid support or material which is insoluble, or can be made insoluble by a subsequent reaction. Numerous and varied solid supports are known to those in the art and include, without limitation, nitrocellulose, the walls of wells of a reaction tray, multi-well plates, test tubes, polystyrene beads, magnetic beads, membranes, and microparticles (such as latex particles). Any suitable porous material with sufficient porosity to allow access by detector reagents and a suitable surface affinity to immobilize capture reagents (e.g., oligonucleotides) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

Target nucleic acid: A defined region or particular portion of a nucleic acid molecule, for example a DNA or RNA of interest. In an example where the target nucleic acid sequence is a target mRNA, such a target can be defined by its specific sequence or function; by its gene or protein name; or by any other means that uniquely identifies it from among other nucleic acids.

In some examples, alterations of a target nucleic acid sequence (e.g., an mRNA) are "associated with" a disease or condition. That is, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by nucleotide polymorphisms (for example, a SNV) or mutation, and/or the two different forms can be quantitatively distinguishable, such as by the number of copies of the target nucleic acid sequence that are present in a sample.

III. NUCLEASE PROTECTION METHODS FOR DETECTING NUCLEOTIDE VARIANTS

Disclosed herein are methods for detecting nucleotide variants in one or more target nucleic acids. The methods disclosed herein can be multiplexed in some embodiments. For example, in some embodiments, two or more (such as 2, 3, 4, 5, 7, 8, 9, 10, 15, 20, 25, 30, 35, 40, 45, 50, or more) different variants can be detected in the same reaction. In some examples, the two or more variants are in the same target nucleic acid or gene. In other examples, the two or more variants are in different target nucleic acids. This is discussed in more detail in Section IV, below.

The disclosed methods can include nuclease protection of variant and/or non-variant (wild type) probes following hybridization to a target nucleic acid (such as a target RNA). In some embodiments, the methods include at least two probes, with one probe forming a perfect hybrid with the wild type (non-variant) sequence and a second probe forming a perfect hybrid with the variant sequence. The probes are designed such that they compete for binding to the same site on the target nucleic acid, particularly at the region including the variant nucleotide position(s), which in some embodiments is about 2 to 8 bases (such as about 3 to 6 bases) from an end of the probe. The probes bind to the same strand of the target nucleic acid, for example, the same RNA strand or the same one strand of a double-stranded molecule, and compete for binding to the same site on the target nucleic acid. Without being bound by theory, it is believed that the probe forming the perfect match with the target nucleic acid will outcompete and exclude at least the portion of the probe including one or more mismatches with the target nucleic acid. The probe forming the perfect match will thus be resistant to nuclease digestion and can be subsequently detected (directly or indirectly). The probe including one or more mismatches will be at least partially single-stranded and will be digested by nuclease, decreasing the amount of this probe that is detected. Alternatively, instead of detecting the probe that survived treatment with the nuclease, the target nucleic acid strand that was hybridized to the probe (such as an RNA or DNA strand) can be detected, for example utilizing one or more detection methods described in Section IV, below (for example, in Section IV(B)). Thus, although detection of probes is referred to throughout, one will appreciate that protected target nucleic acids (such as DNA or RNA) can be substituted therefor. In examples where the target nucleic acid is RNA, the target nucleic acid can be converted to DNA prior to detection.

In some embodiments, the non-variant and variant probes overlap at the 3' end of one probe and at the 5' end of the other probe. An exemplary schematic of an assay with such "offset" (or "competimer") probes is shown in FIG. 1A. The variant nucleotide position(s) are close to the overlapping ends of the probes (for example about 2 to 8 bases from the 3' end of one probe and about 2 to 8 bases from the 5' end of the other probe). In some embodiments, the non-variant probe includes a nucleotide(s) complementary to the non-variant (wild type) nucleotide(s) at the variant position(s), which is near the 3'-end of the probe and the variant probe includes a nucleotide(s) complementary to the variant nucleotide(s) at the variant position(s), which is near the 5'-end of the probe. In other embodiments, the non-variant probe includes a nucleotide(s) complementary to the non-variant (wild type) nucleotide(s) at the variant position(s), which is near the 5'-end of the probe and the variant probe includes a nucleotide(s) complementary to the variant nucleotide(s) at the variant position(s), which is near the 3'-end of the probe. If the variant form of the target nucleic acid is present in the sample, the variant probe forms a perfect match with the target nucleic acid and is protected from nuclease digestion, while the end of the non-variant probe is excluded (either partially or entirely) from hybridization by competition with the variant probe and the excluded end is susceptible to digestion with a nuclease specific for single-stranded nucleic acids. If the non-variant form of the target nucleic acid is present in the sample, the non-variant probe forms a perfect match with the target nucleic acid and is protected from digestion with a nuclease specific for single-stranded nucleic acids, while the end of the variant probe is excluded (either entirely or partially) from hybridization by competition with the non-variant probe and the excluded end is susceptible to nuclease digestion. In some embodiments, the probes are end-labeled, such that nuclease digestion of the mismatched region removes the label and decreases the signal from the mismatched probe. If a mixture of non-variant and variant target nucleic acids is present in the sample, both the non-variant and variant probes will be protected from nuclease digestion in amounts proportional to the amounts of the corresponding non-variant and variant nucleic acids in the sample. Thus, in some examples, the disclosed methods are semi-quantitative or quantitative. Methods of detecting the probes present in the sample following nuclease treatment are discussed in Section IV, below.

In other embodiments, the probes overlap along most (or even all) of their length, with the variant nucleotide position(s) near (for example about 2 to 8 bases from) the same end of both the non-variant probe and the variant probe (either the 5' end of both or the 3' end of both). An exemplary schematic of an assay with such "overlap" probes is shown in FIG. 1B. In some embodiments, each probe is labeled with a different detectable label. If the variant form of the target nucleic acid is present in the sample, the variant probe forms a perfect match with the target nucleic acid and is protected from digestion with a nuclease specific for single-stranded nucleic acids, while the non-variant probe is excluded (either entirely or partially) from hybridization by competition with the variant probe and is susceptible to digestion by a nuclease specific for single-stranded nucleic acids. If the non-variant form of the target nucleic acid is present in the sample, the non-variant probe forms a perfect match with the target nucleic acid and is protected from nuclease digestion, while the variant probe is excluded (either entirely or partially) from hybridization by competition with the non-variant probe and is susceptible to nuclease digestion. In some embodiments, the probes are end-labeled, such that nuclease digestion of the mismatched region removes the label and decreases the signal from the mismatched probe. If a mixture of non-variant and variant target nucleic acids are present in the sample, both the non-variant and variant probes will be protected from nuclease digestion in amounts proportional to the amounts of the corresponding non-variant and variant nucleic acids in the sample. Thus, in some examples, the disclosed methods are semi-quantitative or quantitative. Methods of detecting the probes present in the sample following nuclease treatment are discussed in Section IV, below.

In some embodiments, the methods include contacting a sample (such as a sample including nucleic acids, such as RNA and/or DNA) with at least two probes complementary to a target nucleic acid molecule which includes a nucleotide variant under conditions sufficient for each of the probes to hybridize to the target nucleic acid, producing a mixture of hybridized and unhybridized nucleic acids. In some embodiments, one of the probes (such as the first probe) is complementary to the non-variant sequence for the nucleotide variant and the nucleotide variant position is at least two bases from an end of the probe, and the other probe (such as the second probe) is complementary to the variant sequence for the nucleotide variant and the nucleotide variant position is at least two bases from an end of the probe. Following hybridization, the resulting mixture is treated with a nuclease (such as a nuclease specific for single-stranded nucleic acids, for example S1 nuclease) to remove unhybridized nucleic acid molecules (or unhybridized portions of nucleic acid molecules).

In some examples, the target nucleic acid may include more than one possible sequence at the variant nucleic acid position(s). As a non-limiting example, a target nucleic acid may include a "C" at a nucleotide position in the non-variant nucleic acid and a "G" at the same nucleotide position in a variant nucleic acid. However, in some situations, the target nucleic acid may include a second variant sequence, for example an "A" at the same nucleotide position in a second variant nucleic acid. Therefore, in additional examples, the disclosed methods further include contacting the sample with a third probe which is complementary to the second variant at the variant nucleotide position(s), differing from the non-variant probe and the variant probe. In still further examples, the methods can include contacting the sample with a fourth probe which is complementary to a third variant at the variant nucleotide position(s), differing from the non-variant, variant, and second variant probes. In this way, the disclosed methods can be used to specifically detect the variant sequence present in a sample, even when multiple variants are potentially present (for example, utilizing a different detectable label on each probe). In other examples, the variant probe can include a mixture of all possible variant nucleic acids (for example, the variant probe is degenerate at one or more positions). In a non-limiting example, a non-variant probe includes a "C" at the variant nucleotide position, while the variant probe includes a mixture of "A," "G," and "T" at the variant nucleotide position. In this way, the presence of non-variant or variant target nucleic acid can be detected, although the specific variant sequence is not identified.

In at least some cases, a sample may include a mixture of variant and non-variant (wild-type) target nucleic acids. For example, a sample may include a mixture of cells, some of which include a variant target nucleic acid and others which include the non-variant target nucleic acid (such as a sample including tumor and non-tumor cells). In other examples the sample may include cells in which one allele includes the variant and the other allele includes the non-variant target nucleic acid. The disclosed methods can be used to determine the relative amount of variant and non-variant (wild-type) target nucleic acid present in a sample by determining a ratio of the amount of the variant probe to the amount of the non-variant probe detected following nuclease treatment. For example, if the sample includes 50% variant target nucleic acid and 50% non-variant target nucleic acid, then half of the hybridized (and protected) probe will be the non-variant probe and half of the hybridized (and protected probe) will be the non-variant probe, resulting in approximately a 50/50 ratio of variant to non-variant probe detected.

In other examples, a calibration curve can be produced using varying ratios of variant to non-variant target nucleic acids (such as variant and non-variant IVTs). In one example, a calibration curve is produced using the following ratios of non-variant to variant IVTs: 100/0, 90/10, 80/20, 60/40, 50/50, 40/60, 20/80, 10/90, and 0/100. The ratio of signal from the non-variant to variant probes obtained with each mixture of IVTs is determined. Then the ratio of signal from the non-variant to variant probes obtained in a sample can be calculated and compared to the calibration curve to determine the presence and relative amount of the variant target nucleic acid in the sample.

In some examples, differences in hybridization efficiency, sensitivity to nuclease, or differences in efficiency of detection may lead to different levels of signal from a pair of variant and non-variant probes, even if the same numbers of variant and non-variant nucleic acid molecules are present in a sample. In order to address this issue, a reference probe complementary to the target nucleic acid, but upstream or downstream of the variant nucleic acid position, which does not overlap the variant and non-variant probes, is included in the assay. The reference probe can measure the total amount of the target nucleic acid present in the sample, whether it includes the variant or the non-variant nucleic acid(s). The ratio of the non-variant probe signal to the reference probe signal is determined and the ratio of the variant probe signal to the reference probe signal is determined. These ratios then reflect the proportion of non-variant and variant target nucleic acid present in the sample. In some examples, the reference probe sequence is incorporated into an IVT with the variant and non-variant probes sequences. The IVT thus reflects a model of the actual target nucleic acid and can be used, for example, to construct more accurate calibration curves for a specific assay.

In additional examples, the IVT can be used to adjust assay conditions such that equivalent signal is obtained from each probe. For example, a common nucleic acid sequence that is not related to a target nucleic acid can be incorporated into all IVTs. This "common" sequence is detected by an additional probe and the concentration of each IVT can be adjusted to provide equivalent signal based on the signal from the common probe. Alternatively, instead of physically adjusting the concentration of each IVT, a correction factor can be calculated. Once the IVT concentrations are equal or after using a correction factor to normalize for any inequality of IVT concentration, any difference in signal measured by the variant and non-variant probes is due to differences in efficiency of hybridization and/or detection and the signal can be corrected to produce a measurement of the absolute number of variant and non-variant target nucleic acids, rather than just a relative signal.

A. Reaction Conditions

In the disclosed methods, a sample is contacted with at least two probes under conditions sufficient for each of the probes to hybridize to target nucleic acid present in the sample. The features (such as length, base composition, and degree of complementarity) that will enable a nucleic acid (e.g., a non-variant or variant probe) to hybridize to another nucleic acid (e.g., a target RNA) under conditions of selected stringency, while minimizing non-specific hybridization to other substances or molecules can be determined based on the present disclosure. Characteristics of the probes are discussed in more detail below. Typically, the nucleic acid sequence of a probe will have sufficient complementarity to its corresponding target nucleic acid to enable it to hybridize under selected stringent hybridization conditions, for example hybridization at about 37° C. or higher (such as about 37° C., 42° C., 50° C., 55° C., 60° C., 65° C., 70° C., 75° C., or higher). Among the hybridization reaction parameters which can be varied are salt concentration, buffer, pH, temperature, time of incubation, amount and type of denaturant such as formamide.

In some examples, nucleic acid (e.g., at least two probes) can be added to a sample at a concentration ranging from about 10 pM to about 10 nM (such as about 30 pM to 5 nM, or about 100 pM to about 1 nM), in a suitable buffer such as, for example, 6×SSPE-T (0.9 M NaCl, 60 mM NaH$_2$PO$_4$, 6 mM EDTA, and 0.05% Triton X-100) or lysis buffer (described below). In some examples, each probe is added to the sample at a final concentration of at least 10 pM, such as at least 30 pM, at least 50 pM, at least 80 pM, at least 100 pM, at least 150 pM, at least 200 pM, at least 300 pM, at least 400 pM, at least 500 pM, at least 1 nM, or at least 10 nM. In one example, each probe is added to the sample at a final concentration of about 167 pM. In another example, each probe is added to the sample at a final concentration of about 30 pM. In a further example, each probe is added to the sample at a final concentration of about 1 nM.

The nucleic acids in the sample are denatured (for example at about 95° C. to about 105° C. for about 5-15 minutes) and hybridized to the at least two probes for between about 1-24 hours (for example, at least about 2 hours to about 20 hours, about 4 hours to about 20 hours, about 12 hours to about 18 hours, about 16 hours, or overnight) at a temperature ranging from about 37° C. to about 65° C. (such as about 37, 38, 39, 40, 41, 42, 43, 44, 45, 46, 47, 48, 49, 50, 51, 52, 53, 54, 55, 56, 57, 58, 59, 60, 61, 62, 63, 64, or 65° C.), for example about 50° C. In some examples, the at least two probes are incubated with the sample at a temperature of at least about 37° C., at least about 40° C., at least about 45° C., at least about 50° C., at least about 55° C., at least about 60° C., or at least about 65° C. In one non-limiting example, the at least two probes are incubated with the sample at about 50° C.

In some embodiments, the methods do not include nucleic acid purification (for example, nucleic acid purification is not performed prior to contacting the sample with the probes and/or nucleic acid purification is not performed following contacting the sample with the probes). In some examples, the methods do not include nucleic acid amplification (for example, nucleic acid amplification is not performed prior to contacting the sample with the probes and/or nucleic acid amplification is not performed following contacting the sample with the probes). In some examples, no pre-processing of the sample is required except for cell lysis. In some examples, cell lysis and contacting the sample with the probes occur sequentially. In other examples, cell lysis and contacting the sample with the probes occur concurrently, in some non-limiting examples without any intervening steps.

In the disclosed methods, following hybridization of the at least two probes to the sample, the resulting mixture of hybridized and unhybridized nucleic acid molecules is contacted with a nuclease specific for single-stranded nucleic acids (for example, S1 nuclease) under conditions sufficient to remove the unhybridized (single-stranded) nucleic acid molecules. In some examples, only a portion of one or more of the probes (for example, about 1-10 nucleotides at the 5' or 3' end of the probe) are single-stranded and are susceptible to digestion with the nuclease.

Treatment with one or more nucleases will destroy nucleic acid molecules (or portions thereof) other than the probes which have hybridized to a target nucleic acid present in the sample. For example, if the sample includes a cellular extract or lysate, unwanted nucleic acids, such as genomic DNA, cDNA, tRNA, rRNA, mRNA, and miRNA other than the target nucleic acid of interest and portions of the target nucleic acid of interest that are not hybridized to complementary probe sequences, can be substantially destroyed in this step. Any of a variety of nucleases can be used, including, pancreatic RNAse, mung bean nuclease, S1 nuclease, RNAse A, Ribonuclease T1, Exonuclease III, Exonuclease VII, RNAse CLB, RNAse PhyM, RNAse U2, or the like, depending on the nature of the hybridized complexes and of the undesirable nucleic acids present in the sample. One of ordinary skill in the art can select an appropriate nuclease. In a particular example, the nuclease is specific for single-stranded nucleic acids, for example S1 nuclease. A nuclease specific for single-stranded nucleic acids in some method embodiments disclosed herein permits removal of such single-stranded molecules from subsequent reaction steps where they may lead to undesirable background or cross-reactivity (e.g., false-positive signal). S1 nuclease is commercially available from for example, Promega, Madison, Wis. (cat. no. M5761); Life Technologies/Invitrogen, Carlsbad, Calif. (cat. no. 18001-016); Fermentas, Glen Burnie, Md. (cat. no. EN0321), and others. Reaction conditions for these enzymes are well-known in the art and can be optimized empirically.

In some examples, S1 nuclease diluted in an appropriate buffer is added to the mixture of hybridized and unhybridized nucleic acids and incubated at about 37° C. to about 65° C. (such as about 37, 38, 39, 40, 41, 42, 43, 44, 45, 46, 47, 48, 49, 50, 51, 52, 53, 54, 55, 56, 57, 58, 59, 60, 61, 62, 63, 64, or 65° C.), for example about 50° C. to about 60° C. S1 nuclease is added in an amount sufficient to digest unhybridized (single-stranded) nucleic acid molecules (or portions thereof) present in the mixture, for example about 5-100 U/µl of reaction (for example, about 8 U/µl to about 80 U/µl, about 10 U/µl to about 50 U/µl, or about 20 U/µl to about 40 U/µl). In some examples, about 400-4000 units of S1 nuclease is added to a 50 µl reaction. In one non-limiting example, about 2000 units of S1 nuclease is added to a 50 µl reaction. The nuclease and the mixture of hybridized and unhybridized nucleic acids are incubated for about 10-180 minutes (for example, about 10-60 minutes, about 60-90 minutes, about 90-120 minutes, or about 90-180 minutes) at about 50° C. to 60° C. (such as about 50, 51, 52, 53, 54, 55, 56, 57, 58, 59, or 60° C.). The incubation time can be adjusted depending on the temperature of the nuclease treatment. In some examples, the mixture of hybridized and unhybridized nucleic acids is incubated with S1 nuclease for about 2 hours at 60° C. In other examples, the mixture of hybridized and unhybridized nucleic acids is incubated with S1 nuclease for about 1 hour at 50° C. In still further examples, the mixture of hybridized and unhybridized nucleic acids is incubated with S1 nuclease for about 90 minutes at 37° C. One of ordinary skill in the art can select appropriate times and temperatures for nuclease digestion. Following nuclease treatment, the reaction is stopped, for example by adding a stop solution (for example, a solution including EDTA and NaOH) and heating the sample at about 80-95° C. (such as about 80, 81, 82, 83, 84, 85, 86, 87, 88, 89, 90, 91, 92, 93, 94, or 95° C.) for about 10-20 minutes (for example, about 15 minutes). Additional routine methods for stopping the nuclease reaction can be identified by one of ordinary skill in the art.

The samples can optionally be treated to otherwise remove non-hybridized material and/or to inactivate or remove residual enzymes (e.g., by phenol extraction, precipitation, column filtration, etc.). In some examples, the samples are optionally treated to dissociate the target nucleic acid (such as target RNA) from its complementary probe (e.g., using base hydrolysis and heat). After hybridization, the hybridized target can be degraded, e.g., by nucleases or by chemical treatments, leaving the probes in direct proportion to how much probe had been hybridized to target. Alternatively, the sample can be treated so as to leave the (single strand) hybridized portion of the target, or the duplex formed by the hybridized target and the probe, to be further analyzed.

B. Probes

The disclosed methods include detecting presence of a nucleotide variant in a target nucleic acid molecule. Based on the target nucleic acid molecule and the nucleotide variant in the target nucleic acid, probes can be designed for use in the disclosed methods using the criteria set forth herein in combination with the knowledge of one of ordinary skill in the art.

In the disclosed methods, the probes include a nucleotide (or nucleotides) complementary to wild-type (non-variant) or variant nucleotide (or nucleotides). In some embodiments, the variant nucleotide position(s) is at the end of the probe (such as the 5' end or the 3' end). In other embodiments, the variant nucleotide position(s) is at least two bases from the 5' or 3' end of the probe (such as at least 2, 3, 4, 5, 6, 7, 8, 9, 10, 11, 12, 13, 14, 15, 16, 17, 18, or more bases from the end of the probe). A reference to a nucleotide position that is "2 bases from the end of a probe" refers to the second nucleotide from the end of the probe, a reference to a nucleotide position that is "3 bases from the end of a probe" refers to the third nucleotide from the end of the probe, and so on (that is, the end nucleotide is "1 base from the end" of the probe). FIG. 2 illustrates an exemplary set of "offset" probes in which the variant nucleotide position is 3 bases from the end of the probe. In some examples, the variant nucleotide position is two to eight bases from the end of the probe, for example 2, 3, 4, 5, 6, 7, or 8 bases from the 5' end or 2, 3, 4, 5, 6, 7, or 8 bases from the 3' end of the probe. In one non-limiting example, a variant nucleotide position is three bases from the end of the probe (either the 5' end or the 3' end). In another non-limiting example, a variant nucleotide position is four bases from the end of the probe (either the 5' end or the 3' end). In some examples, the optimal position of the variant nucleotide position(s) may be influenced by the surrounding sequence context of a particular variant. One of ordinary skill in the art can make and test probes with varying positions of the variant nucleotide(s) to determine the optimal position utilizing the teachings of the present disclosure.

Factors that affect probe-target hybridization specificity include probe length, melting temperature, self-complementarity, and the presence of repetitive or non-unique sequence. See, e.g., Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999.

The probes disclosed herein can be selected to include at least 10, at least 15, at least 20, at least 25, or more consecutive nucleotides complementary to a target nucleic acid molecule and including a nucleotide variant position (such as about 6 to 75, 10 to 60, 15 to 50, 18 to 45, 20 to 42, or 23 to 41 consecutive nucleotides complementary to a target nucleic acid molecule). Particular lengths of probes that can be used to practice the methods of the present disclosure include probes having at least 6, 10, 15, 20, 25, 30, 35, 40, 45, 50, or more contiguous nucleotides complementary to a target nucleic acid molecule and including a nucleotide variant position. In a particular non-limiting example, a probe used in the disclosed methods is 15 to 75 (such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75) nucleotides in length.

Conditions resulting in particular degrees of hybridization (stringency) will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. In some examples, the probes utilized in the disclosed methods have a melting temperature ($T_m$, the temperature at which half of the nucleic acid molecules in a mixture are double-stranded and half of the nucleic acid molecules are single-stranded) of at least about 23° C., such as at least about 37° C., at least about 42° C., at least about 45° C., at least about 50° C., at least about 55° C., at least about 60° C., at least about 65° C., at least about 70° C., at least about 75° C., or at least about 80° C., such as about 23° C. to 70° C. (for example, about 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70° C.). In one example, the probes utilized in the disclosed methods have a $T_m$ of about 60° C. to about 70° C. In a particular non-limiting example, the probes utilized in the disclosed methods have a $T_m$ of about 60° C. In some examples, the probes have a $T_m$ of about 59° C. to about 62° C. (such as about 59.1, 59.2, 59.3, 59.4, 59.5, 59.6, 59.7, 59.8, 59.9, 60.0, 60.1, 60.2, 60.3, 60.4, 60.5, 60.6, 60.7, 60.8, 60.9, 61.0, 61.1, 61.2, 61.3, 61.4, 61.5, 61.6, 61.7, 61.8, or 61.9° C.). Methods of calculating the $T_m$ of a probe are known to one of ordinary skill in the art (see e.g., Sambrook et al., *Molecular Cloning: A Laboratory Manual*, 3d ed., Cold Spring Harbor Press, 2001, Chapter 10). Tools for calculating the $T_m$ of a probe are also available on the World Wide Web (such as at promega.com/techserv/tools/biomath/calc11.htm). In some embodiments, the "base-stacking" method is used to calculate probe $T_m$. In some examples, the probes are selected to each have the same or a similar $T_m$ in order to facilitate simultaneous detection of non-variant and/or variant nucleotides in a sample. For example, the probes may be selected to have a $T_m$ within at least 2.5° C. of one another (such as within 2.4° C., 2.3° C., 2.2° C., 2.1° C., 2.0° C., 1.9° C., 1.8° C., 1.7° C., 1.6° C., 1.5° C., 1.4° C., 1.3° C., 1.2° C., 1.1° C., 1.0° C., 0.9° C., 0.8° C., 0.7° C., 0.6° C., 0.5° C., 0.4° C., 0.3° C., 0.2° C., 0.1° C., or less of one another).

In some examples, the probes disclosed herein include one or more synthetic bases or alternative bases (such as inosine). In other examples, the probes disclosed herein include one or more modified nucleotides or nucleic acid analogs, such as one or more locked nucleic acids (see, e.g., U.S. Pat. No. 6,794,499) or one or more peptide nucleic acids. Modified nucleotides, unnatural nucleotides, synthetic, or alternative nucleotides can be used in a probe at one or more positions (such as 1, 2, 3, 4, 5, or more positions). In some examples, use of one or more modified or unnatural nucleotides in the probe can increase the $T_m$ of the probe relative to the $T_m$ of a probe of the same length and composition which does not include the modified nucleic acid. One of ordinary skill in the art can design probes including such modified nucleotides to obtain a probe with a desired $T_m$. Also provided are probes that are degenerate at one or more positions (such as 1, 2, 3, 4, 5, or more positions), for example, a probe that includes a mixture of nucleotides (such as 2, 3, or 4 nucleotides) at a specified position in the probe.

C. Nucleotide Variants

The disclosed methods can be used to detect any type of nucleotide variant (for example, substitution, insertion, duplication, and/or deletion of one or more nucleotides), so long as probes complementary to the variant and non-variant sequences can be designed and synthesized (for example, probes with the properties discussed in Part B, above). The variant sequence may be part of a protein coding sequence and may result in an alteration in one or more amino acids encoded by a nucleic acid sequence (for example, produces one or more amino acid substitutions, insertions, or deletions) or may be a "silent" change, such as a nucleotide variant which does not result in an alteration of the amino acid sequence. The nucleotide may also be in a non-coding region of a nucleotide, including but not limited to an untranslated region or an intron.

In some embodiments, the nucleotide variant is a substitution of one or more nucleotides as compared to the wild-type or non-variant sequence. The nucleotide variant may be a single nucleotide polymorphism (SNP, for example if the target nucleic acid is DNA) or a single nucleotide variant (SNV, for example if the target nucleic acid is RNA), in which the variant is a sequence that varies from the non-variant sequence by only one nucleotide. A non-limiting example of this type of nucleotide variant is as follows:

Non-variant:
ACTGACTG

Variant:
ACTGCCTG

In other examples, the variant is a sequence that varies from the non-variant sequence by two or more nucleotides. The variant sequence may vary from the non-variant sequence by substitution of 2, 3, 4, 5, or more contiguous nucleotides (for example substitution of at least 2 contiguous nucleotides, at least 3, at least 10, or at least 15 contiguous nucleotides, such as 2 to 5, 2 to 10 or 2 to 15 contiguous nucleotides). A non-limiting example of this type of nucleotide variant is as follows:

Non-variant:
ACTGACTGA

Variant:
ACTGCTTGA

In other examples, the variant sequence may vary from the non-variant sequence by substitution of at least 2, at least 3, at least 4, or at least 5 non-contiguous nucleotides, such as 2, 3, 4, 5, or more non-contiguous nucleotides (for example, each substitution is separated from other substitution by at least one nucleotide). A non-limiting example of this type of nucleotide variant is as follows:

Non-variant:
ACTGACTGA

Variant:
AATGCCTGA

In other embodiments, the nucleotide variant is a deletion of one or more nucleotides as compared to the wild-type or non-variant sequence. For example, the nucleotide variant may be a deletion of 1, 2, 3, 4, 5, or more contiguous nucleotides of the target nucleic acid (for example deletion of at least 1 contiguous nucleotide, at least 2, at least 3, at least 10, or at least 15 contiguous nucleotides, such as 1 to 5, 1 to 10, or 1 to 15 contiguous nucleotides). A non-limiting example of this type of nucleotide variant is as follows:

Non-variant:
ACTGACTGA

Variant:
ACTGA-TGA

In some examples, the nucleotide variant is a deletion of three contiguous nucleotides, such as a codon deletion. A non-limiting example of this type of nucleotide variant is as follows:

Non-variant:
ACTGACTGA

Variant:
ACT---TGA

In other examples, the variant sequence may include deletion of at least 2, at least 3, at least 4, at least 5, at least 10, or at least 15 non-contiguous nucleotides, such as 2, 3, 4, 5, or more non-contiguous nucleotides. A non-limiting example of this type of nucleotide variant is as follows:

Non-variant:
ACTGACTGA

Variant:
AC-GAC-GA

In further embodiments, the nucleotide variant is an insertion of one or more nucleotides as compared to the wild-type or non-variant sequence. For example, the nucleotide variant may be an insertion of 1, 2, 3, 4, 5, or more contiguous nucleotides of the target nucleic acid (for example insertion of at least 1, at least 2, at least 3, at least 4, at least 5, at least 10, or at least 15 contiguous nucleotides, such as 1 to 5, 1 to 10, or 1 to 15 contiguous nucleotides). A non-limiting example of this type of nucleotide variant is as follows:

Non-variant:
ACTGA-CTG

Variant:
ACTGAGCTG

In other examples, the variant sequence may include insertion of 2, 3, 4, or more non-contiguous nucleotides (such as insertion of at least 2, at least 3, at least 4, or at least 5 non-contiguous nucleotides, such as 2 to 5, 2 to 10, or 2 to 15 non-contiguous nucleotides). A non-limiting example of this type of nucleotide variant is as follows:

Non-variant:
ACT-GA-CT

Variant:
ACTTGAGCT

In other examples, the nucleotide variant is duplication of one or more nucleotides as compared to the wild-type or non-variant sequence. For example, the nucleotide variant may be duplication of 1, 2, 3, 4, 5, or more contiguous nucleotides of the target nucleic acid (for example duplication of at least 1, at least 2, at least 3, at least 4, at least 5, at least 10, or at least 15 contiguous nucleotides, such as 1 to 5, 1 to 10, 3 to 5, or 1 to 15 contiguous nucleotides). A non-limiting example of this type of nucleotide variant is as follows:

```
Non-variant:
ACT--GACT

Variant:
ACTCTGACT
```

One of ordinary skill in the art can identify additional nucleotide variants that can be detected utilizing the methods disclosed herein, including combinations of one or more of the types of nucleotide variants described above.

In particular non-limiting examples of the methods (such as those described in the Examples, below), a single nucleotide variant resulting in an amino acid substitution is detected. In some examples, the nucleotide variant is in the KRAS coding sequence. In one example, the variant includes an A>C substitution at nucleotide 183 of the KRAS coding sequence, which results in a Gln>His substitution at amino acid 61 (Q61H). In another example, the variant includes a G>A substitution at nucleotide 35 of the KRAS coding sequence, which results in a Gly>Asp substitution at amino acid 12 (G12D). In other examples, the nucleotide variant is in the EGFR coding sequence. In one example, the variant includes a G>T substitution at nucleotide 2527 of the EGFR coding sequence, which results in an Asp>Tyr substation at amino acid 761 (D761Y). In another example, the variant includes a C>T substitution at nucleotide 2615 of the EGFR coding sequence, which results in a Thr>Met substitution at amino acid 790 (T790M). In a further example, the variant includes a T>G substitution at nucleotide 2819 of the EGFR coding sequence, which results in a Leu>Arg substitution at amino acid 858 (L858R). In another example, the variant includes a T>A substitution at nucleotide 1799 of the BRAF coding sequence, which results in a Val>Glu substitution at amino acid 600 (V600E). Exemplary probe sets that can be used to detect these variants are provided in Tables 2 and 9, below (SEQ ID NOs: 1-10 and 15-16). Exemplary variants that can be detected using the methods disclosed herein are shown in Table 1. One of ordinary skill in the art can identify additional variants of interest, including those associated with various diseases and disorders. For example, variants associated with cancer are available on the World Wide Web at cancer.sanger.ac.uk/cancergenome/projects/census.

TABLE 1

Exemplary variants

| Gene | Reference Sequence | Variant Nucleotide Position (Amino acid change) |
|---|---|---|
| KRAS | NM_004985 | 216 G > T (G12V) |
| KRAS | NM_004985 | 216 G > A (G12D) |
| KRAS | NM_004985 | 215 G > T (G12C) |
| KRAS | NM_004985 | 219 G > A (G13D) |
| KRAS | NM_004985 | 363 A > T (Q61L) |
| KRAS | NM_004985 | 364 A/C; 364 A > T (Q61H) |
| BRAF | NM_004333 | 1860 T > A; 1860 TG > AA (V600E) |
| EGFR | NM_005228 | 2527 G > T (D761Y) |
| EGFR | NM_005228 | 2615 C > T (T790M) |
| EGFR | NM_005228 | 2819 T > G (L858R) |
| ER | NM_000125 | 1142 A > G (K303R) |
| FoxL2 | NM_023067 | 820 C > G |
| GNAS | NM_000516 | 960C > T |
| Cldn2 | MGSCv37 X chr | 136339038 C > G |
| Fam120c | MGSCv37 X chr | 147900720 C > T |
| Gprasp1 | MGSCv37 X chr | 132327321 T > C |
| Stard8 | MGSCv37 X chr | 96257763 A > G |
| Apln | MGSCv37 X chr | 45380062 G > A |
| Fmr1 | MGSCv37 X chr | 65969007 A > C |
| Diap2 | MGSCv37 X chr | 126995483 G > C |
| Med14 | MGSCv37 X chr | 12253226 A > T |
| Ddx26b | MGSCv37 X chr | 53749712 A > G |

IV. METHODS OF DETECTION

Following hybridization and nuclease treatment, the probes remaining in the mixture can be detected by any suitable method known in the art or developed hereafter. In some examples, the probes are detected utilizing a capture method (for example, capture of the probes on an array or plurality of beads) or methods that otherwise detect the sequence of the probes. In such methods, at least a portion of the at least two probes have differing sequences, to allow specific capture and discrimination of the probes, for example, utilizing "offset" or "competimer" probes, such as those shown in exemplary FIG. 1A. In other examples, the probes are detected by methods which do not require sequence-specific capture of the probes, for example by utilizing differing detectable labels on each probe. In such examples, the probes can have the same sequence (except for the nucleotide variant position(s)), such as those shown in exemplary FIG. 1B, or can include differing sequences, such as those shown in exemplary FIG. 1A. These methods typically allow multiplexing, or detection of more than one variant in a single assay, for example, where different probes are detected at different spots on an array, in different wells of a multi-well plate, on different beads, in different flow channels, and so on. More than one nucleotide variant may be present in a single nucleic acid target (e.g., RNA) (such as, -nnnV$^1$nnnnnnn$_x$nnnnnnnV$^2$nnnn-, where V$^1$ and V$^2$ are sufficiently spaced to permit a pair of competimer probes at each variant site), or a particular gene may express more than one mRNA variant, each with a different nucleotide at a corresponding position (e.g., EGFR G719(wt), EGFR G719C, EGFR G719S, and/or EGFR G719A; or KRAS G12(wt), KRAS G12D, KRAS G12V, KRAS G12A, KRAS G12R, KRAS G12C, and/or KRAS G12S) or at different positions (e.g., one or more of the foregoing EGFR position 719 forms together with EGFR L858R and/or EGFR T790M), or variants from a plurality of different genes (e.g., one or more of the foregoing EGFR forms together with one or more of the foregoing KRAS forms and/or together with one or more BRAF forms (e.g., V600E)), or a combination of all of the foregoing may be co-detected in a single assay. Additional variants or combinations of variants from the same or different target nucleic acids can be selected. One of ordinary skill in the art can adapt the methods disclosed herein to detect the desired number of variants in a single assay.

A. Detection of Probes Utilizing Sequence-Specific Linkers

In some embodiments, following hybridization and nuclease treatment, the sample is contacted with a surface that includes multiple spatially discrete regions, each including at least one anchor associated with a bifunctional linker (also referred to as a "programming linker"). Alternatively, following hybridization and nuclease treatment, the sample is contacted with a plurality of surfaces, wherein each surface includes at least one anchor associated with a bifunctional linker. For example, the surface can be a population of beads, wherein subpopulations of the beads each include at least one anchor associated with a bifunctional linker. For example a first subpopulation could include at least one anchor associated with a first bifunctional linker, while a second subpopulation could include at least one different anchor associated with a second bifunctional linker, and so on. In another example, the surface can be a flow cell, such as a flow cell with a plurality of channels, wherein subpopulations of the channels each include at least one anchor associated with a bifunctional linker. For example a first subpopulation could include at least one anchor associated with a first bifunctional linker, while a second subpopulation could include at least one different anchor associated with a second bifunctional linker, and so on.

Exemplary methods are disclosed in International Patent Publications WO 99/032663; WO 00/037683; WO 00/037684; WO 00/079008; WO 03/002750; and WO 08/121927; and U.S. Pat. Nos. 6,238,869; 6,458,533; and 7,659,063, incorporated herein by reference in their entirety. See also, Martel et al., *Assay and Drug Development Technologies.* 2002, 1 (1-1):61-71; Martel et al., *Progress in Biomedical Optics and Imaging,* 2002, 3:35-43; Martel et al., *Gene Cloning and Expression Technologies,* Q. Lu and M. Weiner, Eds., Eaton Publishing, Natick (2002); Seligmann, B. *PharmacoGenomics,* 2003, 3:36-43; Martel et al., "Array Formats" in "Microarray Technologies and Applications," U. R. Muller and D. Nicolau, Eds, Springer-Verlag, Heidelberg; Sawada et al., *Toxicology in Vitro,* 20:1506-1513; Bakir, et al., *Biorg. & Med. Chem Lett,* 17: 3473-3479; Kris, et al., *Plant Physiol.* 144: 1256-1266; Roberts, et al., *Laboratory Investigation,* 87: 979-997; Rimsza, et al., *Blood,* 2008 Oct. 15, 112 (8): 3425-3433; Pechhold, et al., *Nature Biotechnology,* 27, 1038-1042. All of these are fully incorporated by reference herein.

The anchor and the bifunctional linker are associated by hybridization, annealing, covalent linkage, or other binding. The bifunctional linker includes a first portion which specifically binds to (for example, is complementary to) at least a portion of the anchor and a second portion which specifically binds to (for example, is complementary to) at least a portion of one of the probes included in the assay (or the region of the target which bound to the probe). In some examples, the sample is sample is treated to inactivate the nuclease (for example, incubating at 95° C. for 15-30 minutes) and neutralized prior to contacting with the surface including the anchor(s) and bifunctional linker(s). The sample is incubated with the surface (for example, an array, bead, or flow cell) for a sufficient period of time for the probes to specifically bind (for example, hybridize) to the bifunctional linkers associated with the anchors. In some examples, the incubation of the sample with the surface is at about 37° C. to about 65° C. (for example, about 45° C. to about 60° C., or about 50° C. to about 60° C., such as 50° C.) for about 1 to 72 hours (for example about 3 to 18 hours, about 12 to 24 hours, about 16 to 24 hours, about 24 to 72 hours, about 24 to 48 hours, about 36 to 72 hours, or overnight) to allow probe hybridization to the bifunctional linker ("probe capture").

In some embodiments, the disclosed methods include an anchor on a surface (for example on an array, bead, or flow cell), which is associated with a bifunctional linker which is utilized to capture the probes following the nuclease step. In some examples, an anchor is an oligonucleotide of about 8 to 150 nucleotides in length (for example, about 15 to 100, 20 to 80, 25 to 75, or 25 to 50, such as about 15, 20, 25, 30, 35, 40, 45, 50, 55, 60, 65, 70, 75, 80, 85, 90, 95, 100, 110, 120, 130, 140, or 150 nucleotides). In one non-limiting example, the anchor is about 25 nucleotides in length. In some examples, the anchor includes a first portion that specifically binds to the first portion of the bifunctional linker and a second portion that acts as a spacer between the surface and the first portion of the anchor. In some examples, the second portion of the anchor is about 6 to 60 carbon atoms or nucleotides in length (such as about 6, 7, 8, 9, 10, 11, 12, 24, 30, 36, 42, 48, 54, or 60 carbon atoms or nucleotides). In other examples, the second portion of the anchor is about 5 to 100 carbon atoms or nucleotides in length (such as about 10 to 50, 15 to 40, 20 to 30, or about 25 carbon atoms or nucleotides).

The base composition for anchors of the disclosed methods is such that the thermodynamic stability of the anchor and bifunctional linker pairing is high. In some examples, the percentage base composition for the anchors is about 30-40% G, 30-40% C, 10-20% A, and 10-20% T. In some examples, nearest neighbor frequency in the anchors minimizes G-G or C-C nearest neighbors to reduce side reactions mediated via G-quartet formation.

Methods of designing and synthesizing anchors of use in the disclosed methods are described, e.g., in PCT Publication No. WO 98/24098, incorporated herein by reference. In some examples, a set of anchors which are substantially dissimilar from one another is desirable. An exemplary algorithm for obtaining a set of dissimilar anchors is as follows:

1) The set size is defined. In some embodiments, 16, 24, 36, 48, 49, 64, 81, 96, and 100 constitute useful sizes.

2) The overall sequence structure of the anchor set is defined. The length and base composition as described above are used to define such parameters. In general, the number of G bases and C bases are held equal as are the number of A bases and T bases. This equality optimizes the configurational diversity of the final sets. Thus, such sets will be described by the equation $G_n C_n A_m T_m$.

3) For a set structure defined by m and n, a random number generator is employed to produce a set of random sequence isomers.

4) One member of the random sequence set is selected to be used as element #1 of the set.

5) The maximum similarity allowable among set members is defined. Similarity is defined in terms of local pair-wise base comparison. For example, when two oligomer strands of identical length n are aligned such that 5' and 3' ends are in register, the lack of mismatches refers to the situation where at all positions 1-n, bases in the two strands are identical. Complete mismatching refers to the situation wherein at all positions 1-n, bases in the two strands are different. For example, a useful maximum similarity might be 10 or more mismatches within a set of 16, 16mer capture probes.

6) A second member of the random sequence set is selected and its similarity to element #1 is determined. If element #2 possesses less than the maximum allowable similarity to element #1, it will be kept in the set. If element #2 possesses greater than the maximum allowable similarity, it is discarded and a new sequence is chosen for comparison. This process is repeated until a second element has been determined.

7) In a sequential manner, additional members of the random sequence set are chosen which satisfy the dissimilarity constraints with respect to all previously selected elements.

Some of the surfaces (or substrates) which can be used in the disclosed methods are readily available from commercial suppliers. In some embodiments, the surface is a 96-, 384-, or 1536-well microtiter plate, such as modified plates sold by Corning Costar or BD Biosciences (for example, gamma-irradiated plates). In other embodiments, a substrate includes one or more beads (such as a population of beads that can be differentiated by size or color, for example by flow cytometry). In some embodiments, a substrate includes a flow cell (such as a flow cell with a plurality of channels). Alternatively, a surface comprising wells which, in turn, comprise indentations or "dimples" can be formed by micromachining a substance such as aluminum or steel to prepare a mold, then microinjecting plastic or a similar material into the mold to form a structure. Alternatively, a structure comprised of glass, plastic, ceramic, or the like, can be assembled. The separator can be, for example, a piece of material, e.g., silicone, with holes spaced throughout, so that each hole will form the walls of a test well when the three pieces are joined. The subdivider can be, for example, a thin piece of material, e.g., silicone, shaped in the form of a screen or fine meshwork. In some examples, the base is a flat piece of material (for example glass or plastic), in, for example, the shape of the lower portion of a typical microplate used for a biochemical assay. The top surface of the base can be flat, or can be formed with indentations that will align with the subdivider shape to provide full subdivisions, or wells, within each sample well. The three pieces can be joined by standard procedures, for example the procedures used in the assembly of silicon wafers.

Suitable materials for the surface include, but are not limited to: glass, silica, gold, silver, a gel or polymer, nitrocellulose, polypropylene, polyethylene, polybutylene, polyisobutylene, polybutadiene, polyisoprene, polyvinylpyrrolidine, polytetrafluroethylene, polyvinylidene difluoride, polyfluoroethylene-propylene, polyethylenevinyl alcohol, polymethylpentene, polycholorotrifluoroethylene, polysulfones, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the surface include: being amenable to surface activation such that upon activation, the surface of the support is capable of covalently (or irreversibly) attaching a biomolecule such as an oligonucleotide thereto; amenability to "in situ" synthesis of biomolecules; being chemically inert such that at the areas on the support not occupied by oligonucleotides or proteins are not amenable to non-specific binding, or when non-specific binding occurs, such materials can be readily removed from the surface without removing the oligonucleotides or proteins.

A wide variety of array formats for arrangement of the anchors can be employed in accordance with the present disclosure. One suitable format includes a two-dimensional pattern of discrete cells (such as 4096 squares in a 64 by 64 array). As is appreciated by one of ordinary skill in the art, other array formats including, but not limited to slot (rect-angular) and circular arrays are equally suitable for use (see U.S. Pat. No. 5,981,185). In some examples, the array is a multi-well plate.

Oligonucleotide anchors, bifunctional linkers, or probes can be synthesized by conventional technology, for example, with a commercial oligonucleotide synthesizer and/or by ligating together subfragments that have been so synthesized. Nucleic acids which are too long to be reliably synthesized by such methods can be generated by amplification procedures, using conventional procedures.

In one embodiment, preformed nucleic acid anchors, such as oligonucleotide anchors, can be situated on or within the surface of a test region by any of a variety of conventional techniques, including photolithographic or silkscreen chemical attachment, disposition by ink jet technology, capillary, screen or fluid channel chip, electrochemical patterning using electrode arrays, contacting with a pin or quill, or denaturation followed by baking or UV-irradiating onto filters (see, e.g., Rava et al. (1996). U.S. Pat. No. 5,545,531; Fodor et al. (1996). U.S. Pat. No. 5,510,270; Zanzucchi et al. (1997). U.S. Pat. No. 5,643,738; Brennan (1995). U.S. Pat. No. 5,474,796; PCT WO 92/10092; PCT WO 90/15070). Anchors can be placed on top of the surface of a test region or can be, for example in the case of a polyacrylamide gel pad, embedded within the surface in such a manner that some of the anchor protrudes from the surface and is available for interactions with a linker. In one embodiment, preformed oligonucleotide anchors are derivatized at the 5' end with a free amino group; dissolved at a concentration routinely determined empirically (e.g., about 1 µM) in a buffer such as 50 mM phosphate buffer, pH 8.5 and 1 mM EDTA; and distributed with a Pixus nanojet dispenser (Cartesian Technologies) in droplets of about 10.4 nanoliters onto specific locations within a test well whose upper surface is that of a fresh, dry DNA Bind plate (Corning Costar). In another embodiment, preformed oligonucleotide anchors are derivatized at the 3' end with a free amino group and include a 7 carbon spacer. Anchor oligonucleotides are dissolved at 20 µM in 0.5 M Phosphate buffer at pH 8.5 and are contact printed on Falcon 1172 plates, gamma irradiated (BD Biosciences) using capillary pins in a humidified chamber. Depending on the relative rate of oligonucleotide attachment and evaporation, it may be required to control the humidity in the wells during preparation. In another embodiment, oligonucleotide anchors can be synthesized directly on the surface of a test region, using conventional methods such as, for example, light-activated deprotection of growing oligonucleotide chains (for example, in conjunction with the use of a site directing "mask") or by patterned dispensing of nanoliter droplets of deactivating compound using a nanojet dispenser. Deprotection of all growing oligonucleotides that are to receive a single nucleotide can be done, for example, and the nucleotide then added across the surface. In another embodiment, oligonucleotide anchors are attached to the surface via the 3' ends of the oligonucleotides, using conventional methodology.

One skilled in the art will appreciate that in some examples, detection using any of the methods provided herein, or even an entire nuclease protection as described herein is performed with a suitably programmed computer or other instrumentation, for example, is automated.

B. Detection of Probes Utilizing Alternative Sequence-Specific Methods

In some embodiments, following hybridization and nuclease treatment the probes in the sample are detected utilizing alternative methods, such as high-throughput platforms. In some examples, probes are detected utilizing conventional microarray analysis or hybrid capture. In some embodiments, the probe does not include a detectable label and indirect detection methods are utilized. Such methods are known to one of ordinary skill in the art and include, but are not limited to, those described below. It is to be understood that detection methods for use in the present disclosure also include novel detection methods developed in the future.

In one example, probes are detected utilizing a bead-based assay, such as a bead array. One example of a bead-based assay utilizes X-MAP® beads (Luminex, Austin, Tex.), such as a QBEAD assay. In some examples, the probes are captured on X-MAP® beads or other beads by hybridization to an oligonucleotide associated with the beads (for example hybridization for about 1-24 hours at about 50° C.). The detectable label included in the probes can be detected, for example by flow cytometry (such as utilizing a Luminex 200, Flexmap 3D, or other suitable instrument) or other suitable detection system (such as biotin/streptavidin).

In another example, probes are detected utilizing a standard microarray. One example of such an array is a Nimblegen microarray (Nimblegen, Madison, Wis.). In some examples, the probes are hybridized to an array including oligonucleotides that specifically bind to the probes. The detectable label included in the probes can be detected, if present.

In further examples, probes are detected with a "bar code" assay. One example of such an assay is nCounter® Analysis System (Nanostring Technologies, Seattle, Wash.). In some examples, following hybridization and nuclease treatment, the probes are hybridized to an oligonucleotide including one or more color coded tags (a "bar-code"). Detection of the color coded tags provides identification of the probes included in the sample. See, e.g., WO 07/0761282; WO 07/076129; WO 07/139766.

In one example, probes are detected using flow cell technology. Exemplary flow cells are available from Advanced Biosensor Technology (Richmond, Va.). In some examples, following hybridization and nuclease treatment, the probes are hybridized to corresponding probes or bifunctional linkers in the channel of a flow cell. The presence of the probe can then be detected using routine methods, such as electrochemical detection, HPLC, or mass spectrometry.

In other examples, probes are detected by mass spectrometry. In further examples, the presence of a full-length probe and label can be differentiated from probes which have been at least partly digested by nuclease based on their size. In other examples, mass spectrometry can be used to detect and differentiate probes based on their size and sequence composition. In still further examples, probes (or the region of the target hybridized to the probe) are detected by sequencing (for example Sanger sequencing, pyrosequencing, reversible dye-terminator sequencing (Illumina sequencing), sequencing by ligation (SOLiD sequencing), semiconductor based sequencing, Helioscope™ sequencing, single molecule sequencing, or nanopore sequencing). In some examples, the probes include one or more flanking sequences at the 5'-end and/or 3'-end of the probe. The flanking sequence(s) includes several contiguous nucleotides having a sequence (such as a sequence of at least 12 nucleotides) not found in a nucleic acid molecule present in the sample, and provide a universal hybridization and/or amplification sequence, which can also be utilized as a universal primer for sequencing of the probe. This universal hybridization and/or amplification sequence, when having a sequence complementary to at least a portion of an amplification primer, permits multiplexing, as the same amplification primers can be used to amplify probes specific for different target nucleic acid molecules. In still further examples, probes are detected by eSensor® technology (GenMark Diagnostics, Carlsbad, Calif.).

C. Detection of Probes Utilizing Differential Labeling

In some embodiments of the disclosed methods, the sample is contacted with at least two probes, each of which include a different detectable label (such as those discussed in Section V, below). The presence of a different detectable label in each probe allows detection of the presence of label (and thus probe) regardless of the sequence of the detected probe. Thus, such detection methods can be utilized in assays wherein the probes include the same sequence, except for the variant nucleotide position(s). Such detection methods can also be utilized in assays wherein the probes include different sequences, except for the overlapping region including the variant nucleotide position(s).

In some embodiments, the at least two probes utilized in the methods are each labeled with a different hapten (such as biotin, digoxigenin, fluorescein, or dinitrophenyl). Following nuclease treatment, the presence and/or amount of each probe can be determined by detecting each of the labels. In some examples, each label is detected by a suitable colorimetric assay, wherein presence of each label results in production of a different color product. In one non-limiting example, one probe is labeled with biotin and can be detected by contacting the biotin-labeled probe with avidin or streptavidin conjugated to horseradish peroxidase and the other probe is labeled with digoxigenin and can be detected by contacting the digoxigenin-labeled probe with an anti-digoxigenin antibody conjugated to alkaline phosphatase. Presence and/or amount of the biotin-labeled probe is determined by conversion of a chromogenic substrate (such as TMB, DAB, or ABTS) by horseradish peroxidase into a colored product (for example, a blue product). Presence and/or amount of the digoxigenin-labeled probe is detected by conversion of a chromogenic substrate by alkaline phosphatase into a different colored product (such as a red product). One of ordinary skill in the art can select appropriate combinations of labels, enzymes, and substrates to detect and differentiate multiple labeled probes present in a mixture.

In other embodiments, the at least two probes utilized in the methods are each labeled with a different fluorescent label. The presence and/or amount of each probe remaining following nuclease treatment can be determined by detecting the fluorescent label(s) remaining in the mixture. Any method of detecting and discriminating fluorescent labels now known or developed in the future can be used. In some examples, following nuclease digestion, the mixture is separated by electrophoresis (such as capillary electrophoresis) and the fluorescent labels are detected, for example utilizing laser-induced fluorescence detection. Suitable electrophoresis and detection systems are commercially available, for example Applied Biosystems 3130 Genetic Analyzer or 3730 DNA Analyzer (Applied Biosystems, Carlsbad, Calif.). In other examples, the probes are captured by sequence-based methods (such as those described above) and are differentiated by the specific emission wavelength of their different fluorescent labels.

In further embodiments, each probe is labeled with a donor fluorophore and an acceptor fluorophore, where the combination of donor and acceptor fluorophores is different for each probe. In some examples, the acceptor fluorophore is at the end of the probe closest to the nucleotide variant position. If the probe does not hybridize, the acceptor fluorophore will be removed by the nuclease and signal will not be detected (or reduced signal will be detected). If the probe hybridizes, the acceptor fluorophore will be protected from the nuclease and signal will be detected. In other examples, the acceptor fluorophore is a quencher, and the quencher is at the end of the probe closest to the nucleotide variant position. If the probe does not hybridize, the quencher will be removed by the nuclease, and signal from the donor fluorophore will be detected. If the probe does hybridize, the quencher will be protected from the nuclease and signal from the donor fluorophore will not be detected.

Additional methods of detecting differently labeled probes include flow cytometry. For example, probes labeled with different fluorescent labels can be captured on beads and differentiated by their emission spectra on flow cytometry.

D. Detection of Probes by Sequencing

In some examples, the probe that survives nuclease protection, or the region of the target hybridized to the probe, can be detected by sequencing. Methods of sequencing a nucleic acid are routine in the art.

V. DETECTABLE LABELS

In some examples, the disclosed probes include one or more detectable labels. Detectable labels are well known in the art. A "detectable label" is a molecule or material that can be used to produce a detectable signal that indicates the presence or concentration of the probe (e.g., the bound or hybridized probe) in a sample. Thus, a labeled nucleic acid molecule provides an indicator of the presence or concentration of a target nucleic acid sequence (e.g., a target nucleic acid having one or more non-variant or variant nucleotides) in a sample. The disclosure is not limited to the use of particular labels, although examples are provided.

In some examples, each of the probes utilized in the disclosed methods are labeled with the same detectable label. In other examples at least one probe is labeled with a different detectable label than at least one other probe utilized in the method. For example, at least one probe (for example, the "wild type" or "non-variant" probe) can be labeled with a fluorophore (such as Cy-3™) and at least one probe (for example, the "variant" probe) can be labeled with a different fluorophore (such as Cy-5™). If additional probes are included in the methods, they can be labeled with the same detectable label as one of the first and second probes, or with a different detectable label than either the first and second probe.

A label associated with one or more nucleic acid molecules (such as a disclosed probe) can be detected either directly or indirectly. A label can be detected by any known or yet to be discovered mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens, radionuclides, and paramagnetic and magnetic molecules or materials. Additional detectable labels include Raman (light scattering) labels (e.g., Nanoplex® biotags, Oxonica, Bucks, UK).

In non-limiting examples, probes are labeled with dNTPs covalently attached to hapten molecules (such as a nitroaromatic compound (e.g., dinitrophenyl (DNP)), biotin, fluorescein, or digoxigenin). Methods for conjugating haptens and other labels to dNTPs (e.g., to facilitate incorporation into labeled probes) are well known in the art. For examples of procedures, see, e.g., U.S. Pat. Nos. 5,258,507, 4,772,691, 5,328,824, and 4,711,955. A label can be directly or indirectly attached to a dNTP at any location on the dNTP, such as a phosphate (e.g., $\alpha$, ($\beta$ or $\gamma$ phosphate) or a sugar. In some examples, detection of labeled nucleic acid molecules can be accomplished by contacting the hapten-labeled probe(s) with a primary anti-hapten antibody. In one example, the primary anti-hapten antibody (such as a mouse anti-hapten antibody) is directly labeled with an enzyme. In another example, a secondary anti-antibody (such as a goat anti-mouse IgG antibody) conjugated to an enzyme is used for signal amplification. In other examples, the hapten is biotin and is detected by contacting the hapten-labeled probe with avidin or streptavidin conjugated to an enzyme, such as horseradish peroxidase or alkaline phosphatase.

Additional examples of detectable labels include fluorescent molecules (or fluorochromes). Numerous fluorochromes are known to those of ordinary skill in the art, and can be selected, for example from Life Technologies (Carlsbad, Calif.), e.g., see, *The Molecular Probes Handbook—A Guide to Fluorescent Probes and Labeling Technologies*. Examples of particular fluorophores that can be attached (for example, chemically conjugated) to a nucleic acid molecule (such as a probe) are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE® dye), fluorescein, fluorescein isothiocyanate (FITC), and QFITC (XRITC), 6-carboxy-fluorescein (HEX), and TET (tetramethyl fluorescein); 2', 7'-difluorofluorescein (OREGON GREEN® dye); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodaminexisothiocyanate, rhodamine green, N,N,N',N'-tetramethyl-6-carboxyrhodamine (TAMRA), tetramethyl rhodamine, and tetramethyl rhodamine isothiocyanate (TRITC); sulforhodamine B, sulforhodamine 101 and sulfonyl chloride derivative of sulforhodamine 101 (Texas Red® dye); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; boron dipyrromethene difluoride (BODIPY); acridine; stilbene; Cy3; Cy5, VIC® dye (Applied Biosystems); LC Red 640; LC Red 705; and Yakima yellow amongst others. Additional examples of fluorophores include Quasar® 670, Quasar® 570, CAL Fluor® Red 590, CAL Fluor® Red 610, CAL Fluor® 615, CAL Fluor® Red 635, CAL Fluor® Green 520, CAL Fluor® Gold 540, and CAL Fluor® Orange 560 (Biosearch Technologies, Novato, Calif.). Other suitable fluorophores include those known to those of ordinary skill in the art, for example those available from Molecular Probes/Life Technologies (Carlsbad, Calif.).

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those one ordinary skill in the art can also be used, for example those available from Life Technologies and including the ALEXA FLUOR® series of dyes (for example, as described in U.S. Pat. Nos. 5,696,157, 6,130,101 and 6,716,979), the BODIPY® series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue® dye (an amine reactive derivative of the sulfonated pyrene described in U.S. Pat. No. 5,132,432) and Marina Blue® dye (U.S. Pat. No. 5,830,912).

In particular examples, a fluorophore is used as a donor fluorophore or as an acceptor fluorophore. "Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHER® dyes (Biosearch Technologies; such as BHQ0, BHQ1, BHQ2, and BHQ3), ECLIPSE™ Dark Quencher (Epoch Biosciences), or IOWA BLACK® dye (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

In addition to the fluorochromes described above, a fluorescent label can be a fluorescent nanoparticle, such as a semiconductor nanocrystal, e.g., a QUANTUM DOT™ (obtained, for example, from Life Technologies); see also, U.S. Pat. Nos. 6,815,064; 6,682,596; and 6,649,138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et al., *Science* 281:2013-2016, 1998; Chan et al., *Science* 281:2016-2018, 1998; and U.S. Pat. No. 6,274,323.

Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 nm, 655 nm, 705 nm, or 800 nm emission wavelengths), which are suitable as fluorescent labels in the probes disclosed herein are available from Life Technologies (Carlsbad, Calif.).

Additional labels include, for example, radioisotopes (such as $^3H$), metal chelates such as DOTA and DPTA chelates of radioactive or paramagnetic metal ions like $Gd^{3+}$, and liposomes.

Detectable labels that can be used with nucleic acid molecules (such as a probe) also include enzymes, for example horseradish peroxidase, alkaline phosphatase, acid phosphatase, glucose oxidase, β-galactosidase, β-glucuronidase, or β-lactamase. Where the detectable label includes an enzyme, a chromogen, fluorogenic compound, or luminogenic compound can be used in combination with the enzyme to generate a detectable signal (numerous of such compounds are commercially available, for example, from Life Technologies, Carlsbad, Calif.). Particular examples of chromogenic compounds include diaminobenzidine (DAB), 4-nitrophenylphosphate (pNPP), fast red, fast blue, bromochloroindolyl phosphate (BCIP), nitro blue tetrazolium (NBT), BCIP/NBT, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

Alternatively, an enzyme can be used in a metallographic detection scheme. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922). Metallographic detection methods also include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

In some embodiments, the detectable label is attached to or incorporated in the probe at the 5'-end or the 3'-end of the probe (e.g., the probe is an end-labeled probe). In other embodiments, the detectable label is attached to or incorporated in the probe at any nucleotide position that can be displaced by hybridization of a "competimer" probe, or that can or is or can be single-stranded due to the presence of a mismatch that will destabilize the end bases due to "breathing" of hybridized bases near the end of the probe. In some examples, the detectable label is attached to or incorporated into the probe within two bases of a nucleotide variant position(s). In one non-limiting example, if a nucleotide variant position is at the third base from the end of a probe, the detectable label can be present on one or more of the first five bases at the same end of the probe.

VI. SAMPLES

The samples of use in the disclosed methods include any specimen that includes nucleic acid (such as genomic DNA, cDNA, viral DNA or RNA, rRNA, tRNA, mRNA, miRNA, oligonucleotides, nucleic acid fragments, modified nucleic acids, synthetic nucleic acids, or the like). In some examples, the disclosed methods include obtaining the sample prior to analysis of the sample. In some examples, the disclosed methods include selecting a subject having a tumor, and then in some examples further selecting one or more target nucleic acids including a nucleotide variant to detect based on the subject's tumor, for example, to determine a diagnosis or prognosis for the subject or for selection of one or more therapies. In other examples, the disclosed methods include selecting a subject having, suspected to have, or likely to develop a disorder or condition (such as a heritable genetic disorder, for example, cystic fibrosis, retinitis pigmentosa, muscular dystrophy, or a disease susceptibility gene variant, for example a BRCA1 or BRCA2 mutation), and then in some examples further selecting one or more target nucleic acids including a nucleotide variant to detect based on the subject's known or suspected condition, for example, to determine a diagnosis or prognosis for the subject or for selection of one or more therapies.

Exemplary samples include, without limitation, cells (such as mammalian cells, plant cells, fungal cells, bacterial cells), viruses, cell lysates, blood smears, cytocentrifuge preparations, cytology smears, bodily fluids (e.g., blood, serum, plasma, saliva, sputum, urine, etc.), tissue samples (e.g., tissue or tumor biopsies, tissue transplants, xenographs), fine-needle aspirates, tissue sections (e.g., cryostat tissue sections and/or paraffin-embedded tissue sections), buccal swabs, cervical swabs, and/or environmental samples (such as food, water, soil, air filter, or water filter samples). In other examples, the sample includes isolated nucleic acid (such as genomic DNA, cDNA, RNA, mRNA) from a subject, for example nucleic acid isolated from cells, cell lysates, blood smears, cytology smears, bodily fluids, tissue biopsies, fine-needle aspirates, and/or tissue sections from a subject. Methods of obtaining a sample from a subject are known in the art. For example, methods of obtaining bodily fluid, tissue, or cell samples are routine. Methods of isolating nucleic acids from samples are also routine. Exemplary samples may be obtained from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis. In particular examples, a biological sample includes a tumor sample, such as a sample containing neoplastic cells.

Exemplary neoplastic cells or tissues may be included in or isolated from solid tumors, including lung cancer (e.g., non-small cell lung cancer, such as lung squamous cell carcinoma), breast carcinomas (e.g. lobular and duct carcinomas), adrenocortical cancer, ameloblastoma, ampullary cancer, bladder cancer, bone cancer, cervical cancer, cholangioma, colorectal cancer, endometrial cancer, esophageal cancer, gastric cancer, glioma, granular call tumor, head and neck cancer, hepatocellular cancer, hydatiform mole, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz nevus, squamous cell cancer, teratoid cancer, and thyroid cancer. Exemplary neoplastic cells may also be included in or isolated from hematological cancers including leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

For example, a sample from a tumor that contains cellular material can be obtained by surgical excision of all or part of the tumor, by collecting a fine needle aspirate from the tumor, as well as other methods known in the art. In some examples, a tissue or cell sample is applied to a substrate and analyzed to determine presence or absence of one or more nucleotide variants. A solid support useful in a disclosed method need only bear the biological sample and, optionally, but advantageously, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

The disclosed methods are sensitive and specific and allow detection of a nucleotide variant in a target nucleic acid in a sample containing even a limited number of cells. For example, presence of one or more nucleotide variants in a target nucleic acid can be detected in as few as 100 cells (such as a sample including 100 or more cells, such as 500, 1000, 2000, 3000, 4000, 5000, 6000, 7000, 8000, 9000, 10,000, 15,000, 20,000, 50,000, or more cells). In some examples, expression of a target nucleic acid (such as a variant target nucleic acid) can be detected in about 1000 to 100,000 cells, for example about 1000 to 50,000, 1000 to 15,000, 1000 to 10,000, 1000 to 5000, 3000 to 50,000, 6000 to 30,000, or 10,000 to 50,000 cells). In other examples, presence of one or more nucleotide variants in a target nucleic acid can be detected in about 1 to 1000 cells (such as about 1 to 500 cells, about 1 to 250 cells, about 1 to 100 cells, about 1 to 50 cells, about 1 to 25 cells, or about 1 cell). In other examples, the disclosed methods allow detection of as few as about 10,000 copies of a nucleotide variant (such as 10,000 or more copies, for example, about 15,000, 25,000, 50,000, 100,000, 150,000, 200,000, 500,000, or more copies) of one or more nucleotide variants in a target nucleic acid in a sample or a reaction (such as a typical 30 µl reaction). In other examples, presence of about 10,000 to 250,000 copies (such as about 10,000 to 100,000 copies, about 15,000 to 150,000 copies, about 20,000 to 200,000 copies or about 100,000 to 250,000 copies) of one or more nucleotide variants in a target nucleic acid can be detected in a sample.

The samples described herein can be prepared using any method now known or hereafter developed in the art. In some examples, cells in the sample are lysed or permeabilized in an aqueous solution (for example using a lysis buffer). The aqueous solution or lysis buffer includes detergent (such as sodium dodecyl sulfate) and one or more chaotropic agents (such as formamide, guanidinium HCl, guanidinium isothiocyanate, or urea). The solution may also contain a buffer (for example SSC). In some examples, the lysis buffer includes about 15% to 25% formamide (v/v) about 0.01% to 0.1% SDS, and about 0.5-6×SSC (for example, about 3×SSC). The buffer may optionally include tRNA (for example, about 0.001 to about 2.0 mg/ml) or a ribonuclease inhibitor. The lysis buffer may also include a pH indicator, such as Phenol Red, EDTA (for example, about 1 mM or less), and/or proteinase K (for example about 0.1 to 2 mg/ml). In a particular example, the lysis buffer includes 20% formamide, 3×SSC (79.5%), 0.05% SDS, 1 µg/ml tRNA, and 1 mg/ml Phenol Red. Cells are incubated in the aqueous solution for a sufficient period of time (such as about 1 minute to about 60 minutes, for example about 5 minutes to about 20 minutes, or about 10 minutes) and at a sufficient temperature (such as about 22° C. to about 115° C., for example, about 37° C. to about 105° C., or about 90° C. to about 100° C.) to lyse or permeabilize the cell. In some examples, lysis is performed at about 95° C. In some examples, the lysis step includes incubating the sample at about 95° C. for about 5-15 minutes to denature RNA in the sample, but not genomic DNA. In other examples, the lysis step includes incubating the sample at about 105° C. for about 5-15 minutes to denature both RNA and genomic DNA in the sample.

In some examples, the crude cell lysis is used directly without further purification ("lysis only" sample preparation). The cells may be lysed in the presence or absence of one or more of the disclosed probes. If the cells are lysed in the absence of probe, the one or more probes can be subsequently added to the crude lysate. In other examples, nucleic acids are isolated from the cell lysate prior to contacting with one or more of the disclosed probes. In some examples, isolated nucleic acids (such as RND or DNA) are added to lysis buffer, and then the one or more probes are subsequently added.

In other examples, tissue samples are prepared by fixing and embedding the tissue in a medium or include a cell suspension prepared as a monolayer on a solid support (such as a glass slide), for example by smearing or centrifuging cells onto the solid support. In other examples, a cell pellet is prepared by sedimenting a population of cells (such as cells obtained from a tissue sample or cultured cells). The cell pellet can further be fixed and embedded in an embedding medium for analysis. In further examples, fresh frozen (for example, unfixed) tissue or tissue sections may be used in the methods disclosed herein. In particular examples, FFPE tissue sections are used in the disclosed methods.

In some examples an embedding medium is used. An embedding medium is an inert material in which tissues and/or cells are embedded to help preserve them for future analysis. Embedding also enables tissue samples to be sliced into thin sections. Embedding media include paraffin, celloidin, OCT™ compound, agar, plastics, or acrylics. Many embedding media are hydrophobic; therefore, the inert material may need to be removed prior to analysis, which utilizes primarily hydrophilic reagents. The term deparaffinization or dewaxing is broadly used herein to refer to the partial or complete removal of any type of embedding medium from a biological sample. For example, paraffin-embedded tissue sections are dewaxed by passage through organic solvents, such as toluene, xylene, limonene, or other suitable solvents. In other examples, paraffin-embedded tissue samples are overlaid with hot mineral oil or NOR-PAR® (ExxonMobil Chemical) and the paraffin partitions into the organic phase with heating and gentle inversion. In further examples, paraffin-embedded tissue sections are utilized directly (e.g., without a dewaxing step).

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing tissue or cell samples is formaldehyde, generally in the form of a formalin solution (4% formaldehyde in a buffer solution, referred to as 10% buffered formalin). In one example, the fixative is 10% neutral buffered formalin.

VII. ASSAY OUTPUT

In some embodiments, the disclosed methods include determining presence or an amount of one or more nucleic acids (such as one or more non-variant or variant nucleic acids) in a sample. The results of the test are provided to a user (such as a scientist, clinician or other health care worker, laboratory personnel, or patient) in a perceivable output that provides information about the results of the test. In some examples, the output can be a paper output (for example, a written or printed output), a display on a screen, a graphical output (for example, a graph, chart, or other diagram), or an audible output. In one example, the output is a table or graph including a qualitative or quantitative indicator of presence or amount (such as a normalized amount or a ratio) of non-variant and/or variant nucleic acid detected (or not detected) in the sample. In other examples the output is a map or image of signal present on a substrate (for example, a digital image of fluorescence or luminescence from an array). In another example, the output is a nucleic acid sequence. In some examples, the output is provided by a suitably programmed computer or other instrumentation.

In some examples, the output is a numerical value, such as an amount of a non-variant or variant nucleic acid in a sample (including, but not limited to a ratio of non-variant to variant nucleic acid or a percentage of non-variant and/or variant nucleic acid in the sample). In additional examples, the output is a graphical representation, for example, a graph that indicates the value (such as amount or relative amount) of a non-variant or variant nucleic acid in the sample on a standard curve. In some examples, the output is communicated to the user, for example by providing an output via physical, audible, or electronic means (for example by mail, telephone, facsimile transmission, email, or communication to an electronic medical record).

The output can provide quantitative information (for example, an amount of a particular non-variant or variant nucleic acid, a ratio of a non-variant to variant nucleic acid in a sample, or an amount of a non-variant or variant nucleic acid relative to a control sample or value) or can provide qualitative information (for example, a determination of presence or absence of a particular non-variant or variant nucleic acid). In some examples, the output is expressed as amount of a variant or non-variant nucleic acid relative to cell number, tissue area, amount of tissue or cells, µg of nucleic acid, volume of sample (for example, volume of blood), or viral, fungal, or bacterial titer. In additional examples, the output can provide qualitative information regarding the relative amount of a non-variant or variant nucleic acid in the sample, such as identifying an increase or decrease relative to a control or no change relative to a control. In other examples, the output can provide a relative amount of a variant or non-variant nucleic acid in a sample relative to a control or housekeeping gene or relative to a region of the target nucleic acid upstream or downstream from the variant nucleic acid position.

The disclosure is further illustrated by the following non-limiting Examples.

EXAMPLES

Example 1

Detection of Nucleotide Variants in In Vitro Transcripts

This example describes detection of single nucleotide variants in IVTs utilizing a quantitative nuclease protection assay method.

Probe sets were designed to detect nucleotide variants in KRAS or epidermal growth factor receptor (EGFR). Probe sequences are provided in Table 2. Wild type probes were each 3' end-labeled with biotin and variant probes were each 5' end-labeled with biotin.

TABLE 2

Probe sets

| Name[a] | Probe Sequence (5'→3') | Length | Tm (° C.) | SEQ ID NO: |
|---|---|---|---|---|
| 3' bSh_Q61_wt | TGGTCCCTCATTGCACTGTACTCCTCTTG | 29 | 60.2 | 1 |
| 5' bSh_Q61H_snp | TCGTGACCTGCTGTGTCGAGAATATCCAA | 29 | 60.1 | 2 |
| 3' bSh_D761_wt | GCTGGCCATCACGTAGGCTTCATCGA | 26 | 60.3 | 3 |
| 5' bSh_D761Y_snp | ATAGAGGATTTCCTTGTTGGCTTTCGGAGATGT | 33 | 60.8 | 4 |
| 3' bSh_T790_wt | AGCCGAAGGGCATGAGCTGCGTG | 23 | 60.3 | 5 |
| 5' bSh_T790M_snp | GCATGATGAGCTGCACGGTGGAGGT | 25 | 60.5 | 6 |
| 3' bSh_L858_wt | CCGCACCCAGCAGTTTGGCCAGC | 23 | 59.5 | 7 |
| 5' bSh_L858R_snp | CCCGCCCAAAATCTGTGATCTTGACATGC | 29 | 60.8 | 8 |
| 3' bSh_G12_wt | CAAGGCACTCTTGCCTACGCCACCA | 25 | 60.4 | 9 |
| 5' bSh_G12D_snp | CATCAGCTCCAACTACCACAAGTTTATATTCAGTCA | 36 | 60.2 | 10 |

[a]3' bSh indicates that the probe is 3' end-labeled with biotin and 5' bSh indicates that the probe is 5' end-labeled with biotin.
The variant nucleotide position is indicated by bold and underlining in each probe.

Synthetic IVT mRNAs for each wild type or variant sequence were synthesized. Each IVT was diluted to the desired concentration in lysis buffer and 25 µl was added to each well of a 96 well plate, followed by 5 µl of biotinylated probe mix at 1 nM in lysis buffer and 70 µl of denaturation oil. The final concentration of each biotinylated probe was 167 pM. The plate was heated at 95° C. for 10-15 minutes and then incubated at 50° C. for about 16 hours (overnight) to allow IVT-probe hybridization. Following hybridization, 50 units of S1 nuclease (in 20 µl of S1 nuclease buffer) was added and the plate was incubated at 50° C. for 60-90 minutes with shaking to digest unbound IVT and probe. The S1 nuclease reaction was stopped by transferring the entire contents of each well to a new 96-well plate containing 10 µl stop solution per well. This plate was incubated for 15 minutes at 90° C. and allowed to cool for about 15 minutes at room temperature. The reaction was neutralized by the addition of 10 µl of Neutralization Solution and then transferred to a Programmed ArrayPlate™

The ArrayPlate™ included a 4×4 grid of 16 unique "anchor" oligonucleotides spotted in each well, which had been modified to bind "programming linkers" which include a sequence complementary to an anchor and a sequence complementary to one of the probes. The reaction in the ArrayPlate™ was incubated at 50° C. for about 16 hours (overnight) to allow probe hybridization to the programming linkers. The ArrayPlate™ was washed, then incubated with Avidin-Peroxidase at 37° C. for 1 hour. After a final wash, Luminescent Substrate was added to each well and the image was captured on HTG's Omix Imager.

For all probes, signal could be detected with as little as 15,000 copies (1 fM) of IVT per well (Table 3). The assay exhibited linearity across 3 orders of magnitude, from 15 million copies (1 pM) to 15,000 copies (1 fM) of IVT per well (FIG. 3) with R-squared values>0.900. The assay also showed good reproducibility (Table 4) with a coefficient of variation (CV) generally less than 15%.

TABLE 3

IVT titration and average (n = 4) probe signal intensity

| | Conc. (M) | | | | | | |
|---|---|---|---|---|---|---|---|
| | 1E−12 | 3.16E−13 | 1E−13 | 3.16E−14 | 1E−14 | 3.16E−15 | 1E−15 |
| | | | | Copy No. | | | |
| | 15,055,000 | 4,760,926 | 1,505,574 | 476,116 | 150,565 | 47,614 | 15,057 |
| 3'Q61H | 39182 | 14735 | 4265 | 1432 | 481 | 144 | 93 |
| 3'D761Y | 49119 | 16131 | 5636 | 1928 | 587 | 191 | 121 |
| 3'T790M | 9921 | 3432 | 1170 | 352 | 150 | 48 | 96 |
| 3'6858R | 42298 | 17428 | 5060 | 1750 | 527 | 196 | 94 |
| 3'G12D | 60488 | 18124 | 6089 | 1795 | 647 | 221 | 139 |
| 5'Q61H | 10661 | 3597 | 1190 | 324 | 90 | 58 | 49 |
| 5'D761Y | 60068 | 20861 | 7784 | 2297 | 867 | 300 | 168 |
| 5'T790M | 60068 | 35281 | 10986 | 3845 | 1191 | 460 | 259 |
| 5'L858R | 53424 | 10531 | 3597 | 1096 | 365 | 110 | 69 |
| 5'KG12D | 60068 | 18906 | 6165 | 1793 | 565 | 173 | 70 |

| | Conc. (M) | | | | | |
|---|---|---|---|---|---|---|
| | 3.16E−16 | 1E−16 | 3.16E−17 | 1E−17 | 0E0 | |
| | | | Copy No. | | | |
| | 4762 | 1506 | 476 | 151 | 0 | RSQ |
| 3'Q61H | | | | | | 0.9966 |
| 3'D761Y | | | | | | 0.9997 |
| 3'T790M | | | | | | 0.9992 |
| 3'6858R | | | | | | 0.9913 |
| 3'G12D | | | | | | 0.9997 |
| 5'Q61H | | | | | | 0.9995 |
| 5'D761Y | | 74 | 66 | 57 | | 0.9986 |
| 5'T790M | 134 | 87 | 89 | 65 | 56 | 0.9344 |
| 5'L858R | | | | | | 0.9859 |
| 5'KG12D | | | | | | 1.000 |

3' probes are wild type probes and were hybridized with wild type IVTs.
5' probes are variant probes and were hybridized with variant IVTs.

TABLE 4

Coefficients of variation for average (n = 4) probe signal intensity on IVT titration

| | Conc. (M) | | | | | | | | | | | |
|---|---|---|---|---|---|---|---|---|---|---|---|---|
| | 1E−12 | 3.16E−13 | 1E−13 | 3.16E−14 | 1E−14 | 3.16E−15 | 1E−15 | 3.16E−16 | 1E−16 | 3.16E−17 | 1E−17 | 0E0 |
| | | | | | | Copy No. | | | | | | |
| | 15,055,000 | 4,760,926 | 1,505,574 | 476,116 | 150,565 | 47,614 | 15,057 | 4762 | 1506 | 476 | 151 | 0 |
| 3'Q61H | 5% | 4% | 9% | 9% | 9% | 13% | 15% | | | | | |
| 3'D761Y | 8% | 6% | 7% | 8% | 10% | 24% | 8% | | | | | |
| 3'T790M | 3% | 6% | 7% | 5% | 8% | 12% | 40% | | | | | |
| 3'6858R | 5% | 6% | 2% | 12% | 15% | 25% | 21% | | | | | |
| 3'G12D | 11% | 4% | 7% | 19% | 14% | 14% | 12% | | | | | |
| 5'Q61H | 9% | 9% | 6% | 8% | 18% | 4% | 12% | | 2% | 8% | 36% | |
| 5'D761Y | 4% | 6% | 7% | 8% | 11% | 7% | 7% | 31% | 10% | 11% | 41% | 16% |
| 5'T790M | 4% | 11% | 12% | 18% | 12% | 6% | 9% | | | | | |
| 5'L858R | 13% | 13% | 17% | 5% | 33% | 24% | 1% | | | | | |
| 5'KG12D | 4% | 15% | 7% | 22% | 17% | 34% | 20% | | | | | |
| Average | 7% | 8% | 8% | 11% | 15% | 16% | 14% | 31% | 6% | 9% | 39% | 16% |

3' probes are wild type probes and were hybridized with wild type IVTs.
5' probes are variant probes and were hybridized with variant IVTs.

Example 2

Detection of Wild Type and Variant Nucleic Acids in a Sample

This example describes detection of wild type and variant nucleic acids in the same sample using a competitive quantitative nuclease protection assay method.

The methods were carried out as described in Example 1, except that a mixture of both the wild type and variant probe for each SNP was added to a single well and the assay also included a mixture of wild type and variant IVTs.

Alternatively, the starting sample was a lung FFPE sample which was spiked with a mixture of wild type and variant IVTs. In this case, the FFPE sample was scraped off the slide into a centrifuge tube, lysis buffer and denaturation oil were added and the sample was centrifuged for 1 minute at 14,000 rpm. The sample was incubated at 95° C. for 15 minutes and allowed to cool at room temperature for 5-10 minutes. The IVT and 20 mg/ml proteinase K per 100 µl of lysis buffer was added and the sample was incubated at 50° C. with shaking for 30-60 minutes. At this point, 25 µl of the sample was transferred to a 96 well plate and the protocol in Example 1 was followed.

The variant probes showed a high level of specificity of detection (Tables 5-8). For mixtures of wild-type and variant IVTs, a significant difference ($p<0.05$) in signal intensity was observed for all probe sets when 16% variant IVT was present. Some probe sets (D761Y and L858R) showed significant difference in intensity when only 6% variant IVT was present (Table 6). For lung FFPE spiked with a mixture of wild-type and variant IVT, a significant difference ($p<0.05$) in signal intensity was observed for all probe sets when 16% variant IVT was present in the lung FFPE. Some probe sets (Q61H, D761Y, T790M, L858R) showed significant difference in intensity when only 6% variant IVT was present (Table 8).

TABLE 5

Mixed wild type and variant IVT titration (average signal intensity, normalized to all, weighted (n = 4))

| | wild type/% var. IVT | | | | | | | |
|---|---|---|---|---|---|---|---|---|
| | 0/100 | 37/63 | 60/40 | 75/25 | 84/16 | 90/10 | 94/6 | 100/0 |
| 3'EGFR_wt | 5542 | 5432 | 5684 | 5284 | 5125 | 4095 | 5094 | 3865 |
| 3'Q61H_wt | 1265 | 2264 | 3039 | 2817 | 4081 | 2496 | 4097 | 3628 |
| 5'Q61H_SNP | 6060 | 3239 | 2204 | 1257 | 1219 | 644 | 819 | 601 |
| 3'D761Y_wt | 166 | 1956 | 3383 | 3082 | 4562 | 4158 | 4894 | 5000 |
| 5'D761Y_SNP | 8368 | 5569 | 4028 | 2381 | 2419 | 1437 | 1676 | 1050 |
| 3'T790M_wt | 201 | 504 | 819 | 700 | 861 | 601 | 1042 | 1125 |
| 5'T790M_SNP | 13512 | 10224 | 8646 | 5910 | 5403 | 4594 | 4166 | 3775 |
| 3'L858R_wt | 1051 | 2836 | 4172 | 4865 | 5684 | 4714 | 5860 | 5227 |
| 5'L858R_SNP | 5294 | 2220 | 1442 | 745 | 739 | 375 | 457 | 301 |
| 3'G12D_wt | 289 | 2054 | 3812 | 3540 | 4469 | 2924 | 5050 | 4596 |
| 5'KG12D_SNP | 6496 | 4427 | 3325 | 2089 | 2006 | 1054 | 1374 | 1011 |

TABLE 6

T-test for wild-type/variant SNP detection from Table 5

| | % wild type/% var. IVT | | | | | | | |
|---|---|---|---|---|---|---|---|---|
| | 0/100 | 37/63 | 60/40 | 75/25 | 84/16 | 90/10 | 94/6 | 100/0 |
| 5'Q61H_SNP | 0.0077 | 0.0005 | 0.0174 | 0.0033 | 0.0029 | 0.4748 | 0.0658 | |
| 5'D761Y_SNP | 0.0023 | 0.0002 | 0.0012 | 0.0000 | 0.0004 | 0.0008 | 0.0051 | |
| 5'T790M_SNP | 0.0167 | 0.0000 | 0.0001 | 0.0045 | 0.0026 | 0.1301 | 0.1977 | |
| 5'L858R_SNP | 0.0042 | 0.0122 | 0.0000 | 0.0000 | 0.0000 | 0.0000 | 0.0085 | |
| 5'KG12D_SNP | 0.0119 | 0.0000 | 0.0000 | 0.0002 | 0.0002 | 0.7708 | 0.0193 | |

TABLE 7

Mixed wild-type and variant IVT titration spiked into lung FFPE (average signal intensity, normalized to all, weighted (n = 4))

| | % wild type/% var. IVT | | | | | | | |
|---|---|---|---|---|---|---|---|---|
| | 0/100 | 37/63 | 60/40 | 75/25 | 84/16 | 90/10 | 94/6 | 100/0 |
| 3'GAPDH | 1499 | 782 | 1437 | 1329 | 1367 | 1304 | 1216 | 1084 |
| 3'EGFR_wt | 6904 | 4477 | 8034 | 6050 | 8024 | 6100 | 7019 | 4474 |
| 3'Q61H_wt | 1733 | 2084 | 4720 | 4893 | 5831 | 5028 | 5875 | 4866 |
| 5'Q61H_SNP | 7426 | 3011 | 3116 | 1719 | 1318 | 825 | 786 | 495 |
| 3'D761Y_wt | 191 | 1652 | 5247 | 5260 | 6914 | 5807 | 7405 | 3973 |
| 5'D761Y_SNP | 9274 | 5025 | 5555 | 3651 | 2984 | 1977 | 1812 | 1205 |
| 3'T790M_wt | 215 | 411 | 1567 | 1520 | 1945 | 1001 | 1695 | 1459 |
| 5'T790M_SNP | 18863 | 8233 | 11439 | 7973 | 7320 | 5739 | 5658 | 4427 |
| 3'L858R_wt | 1783 | 2832 | 7647 | 7513 | 10009 | 8917 | 9084 | 9048 |

TABLE 7-continued

Mixed wild-type and variant IVT titration spiked into lung FFPE (average signal intensity, normalized to all, weighted (n = 4))

| | % wild type/% var. IVT | | | | | | | |
|---|---|---|---|---|---|---|---|---|
| | 0/100 | 37/63 | 60/40 | 75/25 | 84/16 | 90/10 | 94/6 | 100/0 |
| 5'L858R_SNP | 5103 | 1978 | 2207 | 915 | 863 | 603 | 442 | 280 |
| 3'G12D_wt | 587 | 1840 | 5884 | 6555 | 7212 | 7215 | 7136 | 6503 |
| 5'KG12D_SNP | 7331 | 4386 | 4999 | 2901 | 2591 | 1757 | 1946 | 1824 |

TABLE 8

T-test for wild-type/variant SNP detection from Table 7

| | % wild type/% var. IVT | | | | | | |
|---|---|---|---|---|---|---|---|
| | 0/100 | 37/63 | 60/40 | 75/25 | 84/16 | 90/10 | 94/6 | 100/0 |
| 5'Q61H_SNP | 0.0013 | 0.0336 | 0.0001 | 0.0049 | 0.0074 | 0.0019 | 0.0010 | |
| 5'D761Y_SNP | 0.0000 | 0.0812 | 0.0038 | 0.0021 | 0.0001 | 0.0111 | 0.0008 | |
| 5'T790M_SNP | 0.0041 | 0.0824 | 0.0000 | 0.0236 | 0.0022 | 0.0297 | 0.0089 | |
| 5'L858R_SNP | 0.0374 | 0.0177 | 0.0000 | 0.0000 | 0.0000 | 0.0000 | 0.0237 | |
| 5'KG12D_SNP | 0.0006 | 0.0834 | 0.0001 | 0.0013 | 0.0062 | 0.7550 | 0.5153 | |

Example 3

Detection of Variants in Cell Lines

This example describes detection of variants in samples from cell lines known to include KRAS and/or EGFR mutations utilizing a quantitative nuclease protection assay method.

The starting samples were cells from cell lines known to include one or more EGFR mutations (H1975 and 11-18 cells) as well as a cell line with no known EGFR mutations (A549 cells). 20,000 cells in 25 μl of Lysis Buffer were transferred to a 96 well plate and the protocol in Example 1 was followed. A standard curve consisting of varying ratios of wild-type to variant EGFR IVT was also run on the same plate to serve at a quantitative control.

Figure 4A:
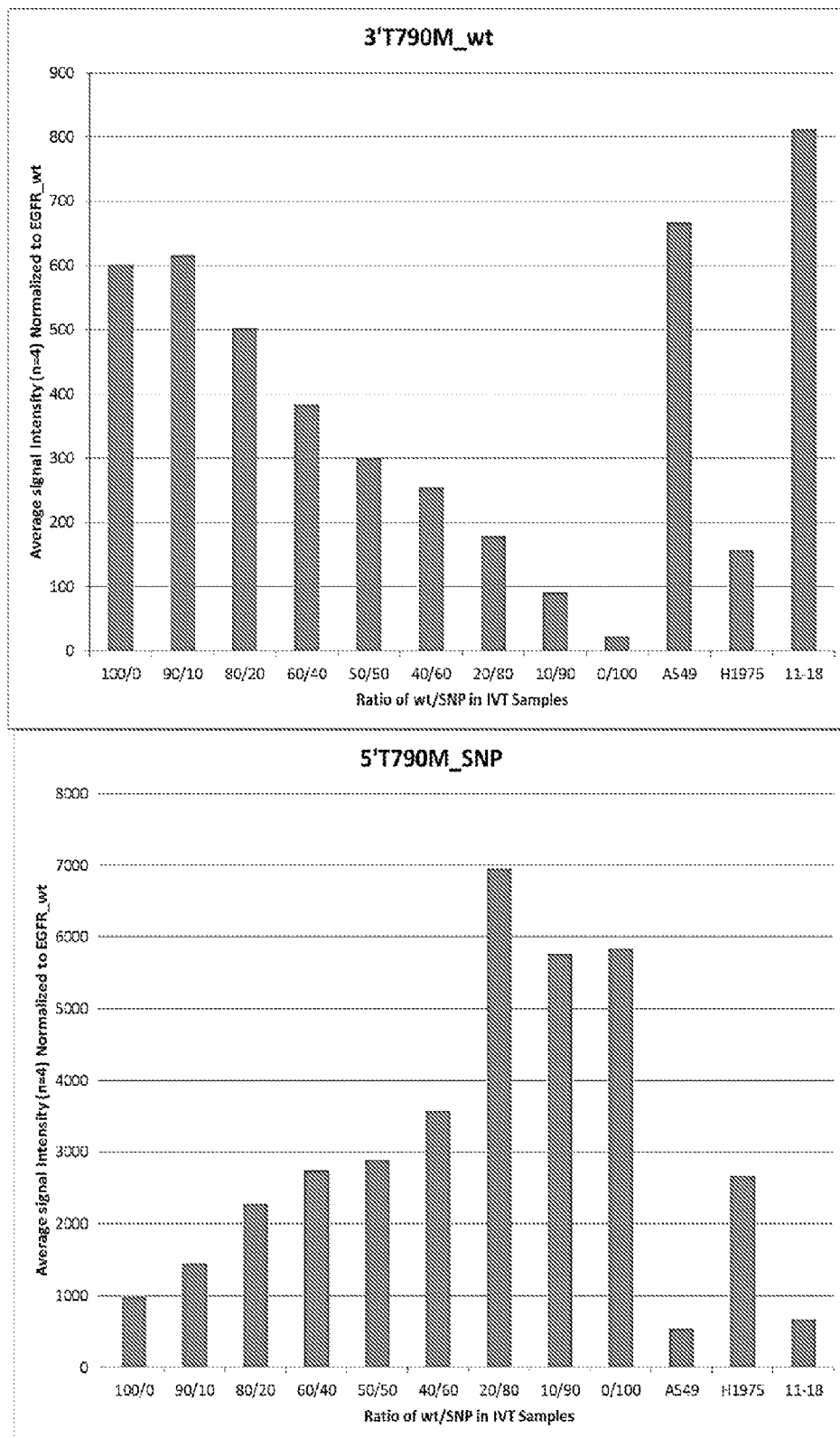
FIG. 4A is a pair of graphs showing wild type (top) and variant (bottom) probe signal for EGFR T790M probes in IVT mixtures and the indicated cell lines.

The A549 cell line (human lung carcinoma, ATCC Number CCL-185) has no known EGFR mutations (Tracy et al., *Cancer Res.* 64:7241-7244, 2004), and as such may serve as a wild type cell control. The H1975 (Human Lung Adenocarcinoma, ATCC Number: CRL-5908) cell line is reported to have both T790M and L858R EGFR mutations at approximately a 50-50 mixture of alleles (Sordella et al., *Science* 305:1163-1167, 2004). The 11-18 cell line has been reported to have the L858R EGFR mutation but not the T790M EGFR Mutation (Nagai et al., *Cancer Res.* 65:7276-7282, 2005). The assay showed that the A549 cell line was wild type for EGFR T790 and L858 (FIGS. 4A and B). The H1975 cell line expressed about 50% T790M and 50% L858R (FIGS. 4A and B) and the 11-18 cell line was wild type for T790, but expressed about 50% L858R (FIGS. 4A and B). The amount of the variant RNA expressed in the cell line sample was estimated from a titration of ratios of wild type to variant IVTs assessed under the same conditions as the cell line samples.

Example 4

Detection of BRAF V600E Variant in Multiple Sample Types

This example describes detection of BRAF V600E variant in IVTs, cell lysates, cell pellets, and FFPE melanoma samples.

A probe set was designed to detect the V600E variant in BRAF. Probe sequences are provided in Table 9. The wild type probe was 3' end-labeled with biotin and the variant probe was 5' end-labeled with biotin.

TABLE 9

BRAF V600E probe set

| Name[a] | Probe Sequence (5'→3') | Length | Tm (° C.) | SEQ ID NO: |
|---|---|---|---|---|
| 3' bR_V600wt | GATGGGACCCACTCCATCGAGATTTCACTG | 30 | 61.2 | 15 |
| 5' bR_V600E | TTCTCTGTAGCTAGACCAAAATCACCTATTTTTACTGTGAG | 41 | 61.7 | 16 |

[a]3' bR indicates that the probe is 3' end-labeled with biotin and 5' bR indicates that the probe is 5' end-labeled with biotin.
The variant nucleotide position is indicated by bold and underlining in each probe.

Figure 5:
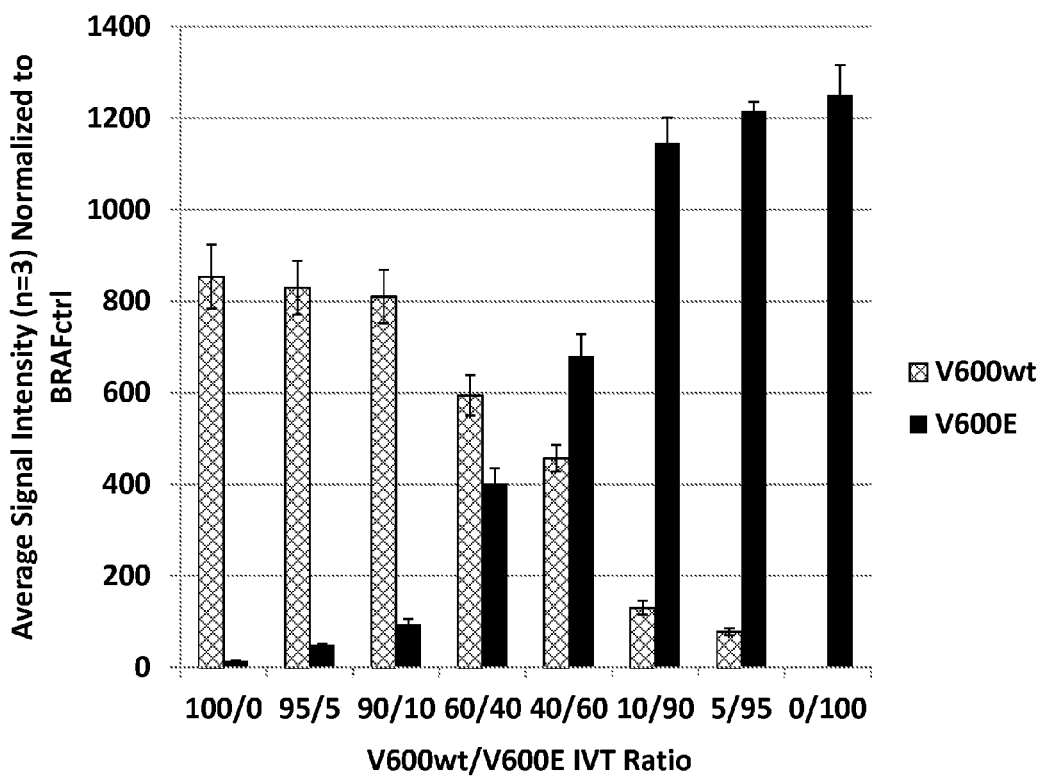
FIG. 5 is a graph showing average signal intensity at varying ratios of BRAF V600 wild type and V600Evariant IVTs detected in the same well. Total IVT was held constant at 200 fM.

Detection of varying amounts of mixed BRAF wild type and V600E IVTs was carried out as described in Example 2. A mixture of both the wild type and variant probe for the BRAF V600E SNP was added to a single well and the assay also included either V600 wild type or V600E IVT alone or as a mixture of wild type and variant IVTs. Total IVT concentration was held constant at 200 fM. The V600E mutation could be detected even when present at only 5% of the total transcript amount (FIG. 5).

Figure 6:
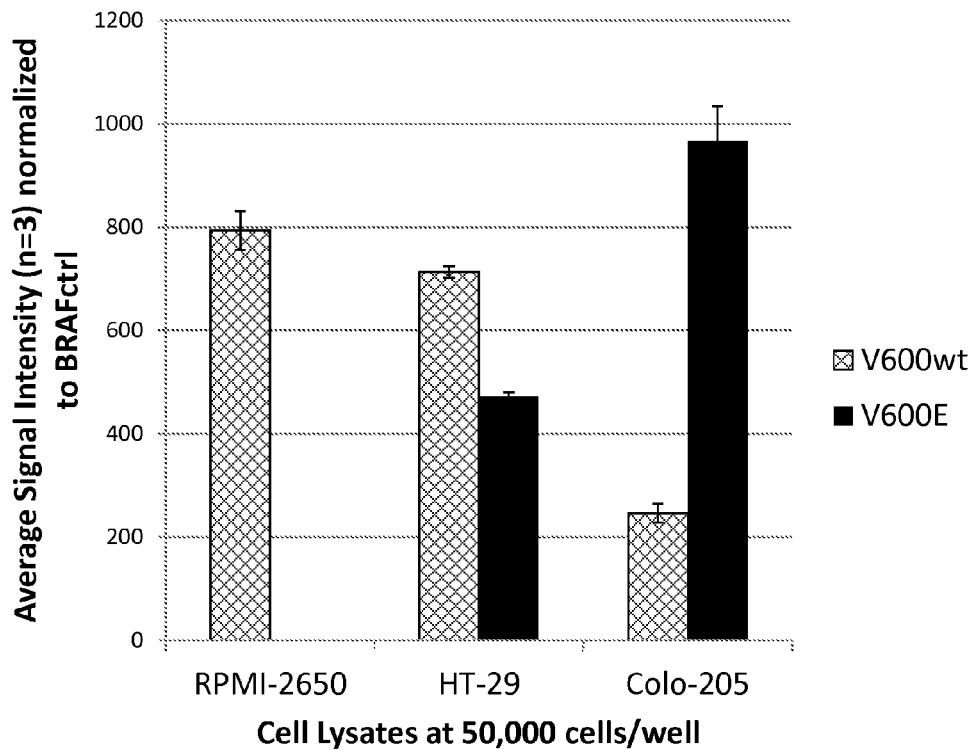
FIG. 6 is a graph showing average signal intensity of V600 wild type and V600E probes in cell lysates from the indicated cell lines.

Presence of BRAF V600E was assayed in cell lysates from cell lines known to include the mutation utilizing a quantitative nuclease protection assay method. The protocol described in Example 3 was followed, except that the cell lysates were prepared from 50,000 cells and S1 nuclease reaction was carried out at 60° C. The starting samples were cells from colon cancer cell lines known to be heterozygous for the BRAF V600E variant (HT-29 and COLO-205; www.atcc.org/~/media/PDFs/Culture %20Guides/Cell_Lines_by_Gene_Mutation.ashx) as well as a squamous cell carcinoma cell line wild type at BRAF amino acid 600 (RPMI-2650). Using the V600 wt and V600E probes, BRAF V600E variant and wild type were both detected in the known heterozygous cell lines, while only wild type was detected in the RPMI-2650 cell line (FIG. 6).

Figure 7:
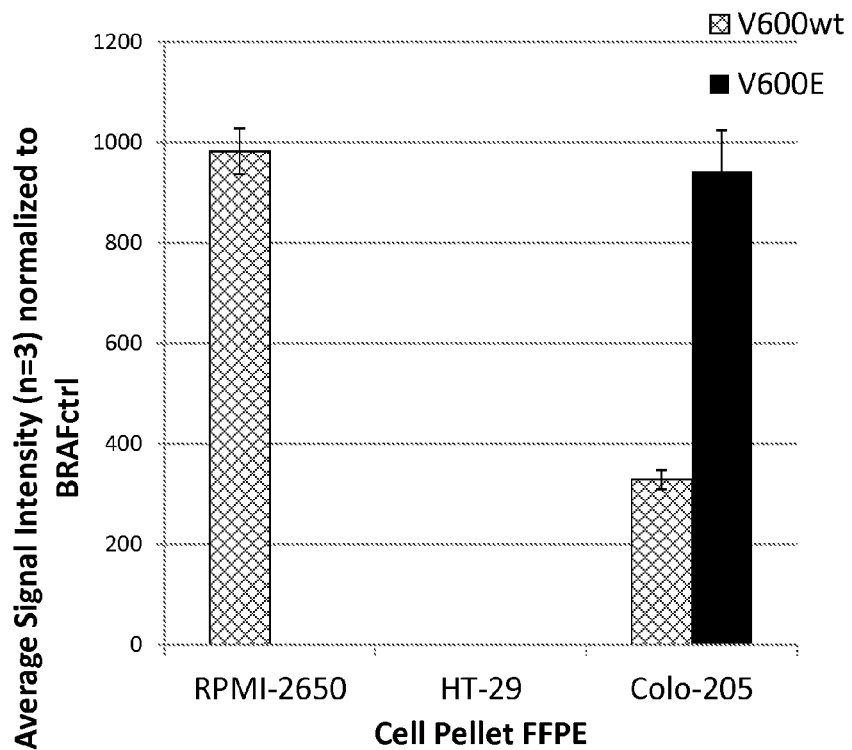
FIG. 7 is a graph showing average signal intensity of V600 wild type and V600E probes in formalin-fixed paraffin embedded (FFPE) cell pellets from the indicated cell lines.

Fixed cell pellets were also prepared and used as samples in the assays. Cell pellets were prepared by centrifuging 8-15×10$^6$ cells, removing the supernatant, and repelleting the cells in 1-4 ml PBS. The cell pellet was fixed for at least 4 hours in cold 10% neutral buffered formalin. The cells were then centrifuged at 1500 rpm for 5 minutes and the supernatant was removed. Cell blocks were prepared using Shandon CYTOBLOCK® cell block preparation system (Thermo Scientific, Waltham, Mass.). Briefly, 1-2 drops of Reagent #2 was added to pelleted cells in a 15 ml conical tube, with vortexing. Next, 1-2 drops of Reagent #1 was mixed with the cells. The gelled cell block was transferred to a cassette and placed in 70% alcohol. The FFPE cell pellet blocks were cut into 5 micron sections on a microtome. The area of the cell pellet was approximately 1 cm$^2$. Lysis Buffer (25 µL) was added for each 5 µm section. The samples were then heated to 95° C. and treated with proteinase K as described in Example 2 above. In this experiment the samples were tested at a concentration of one 5 µm section per well. The nuclease protection assay was carried out according to the protocol in Example 1. Only wild type BRAF V600 was detected in RPMI-2650 cells, while both wild type and V600E variant were detected in the COLO-205 cells (FIG. 7). Neither was detected in the HT-29 cell pellet. This was likely due to a problem in the sample preparation of this cell pellet.

Figure 8A:
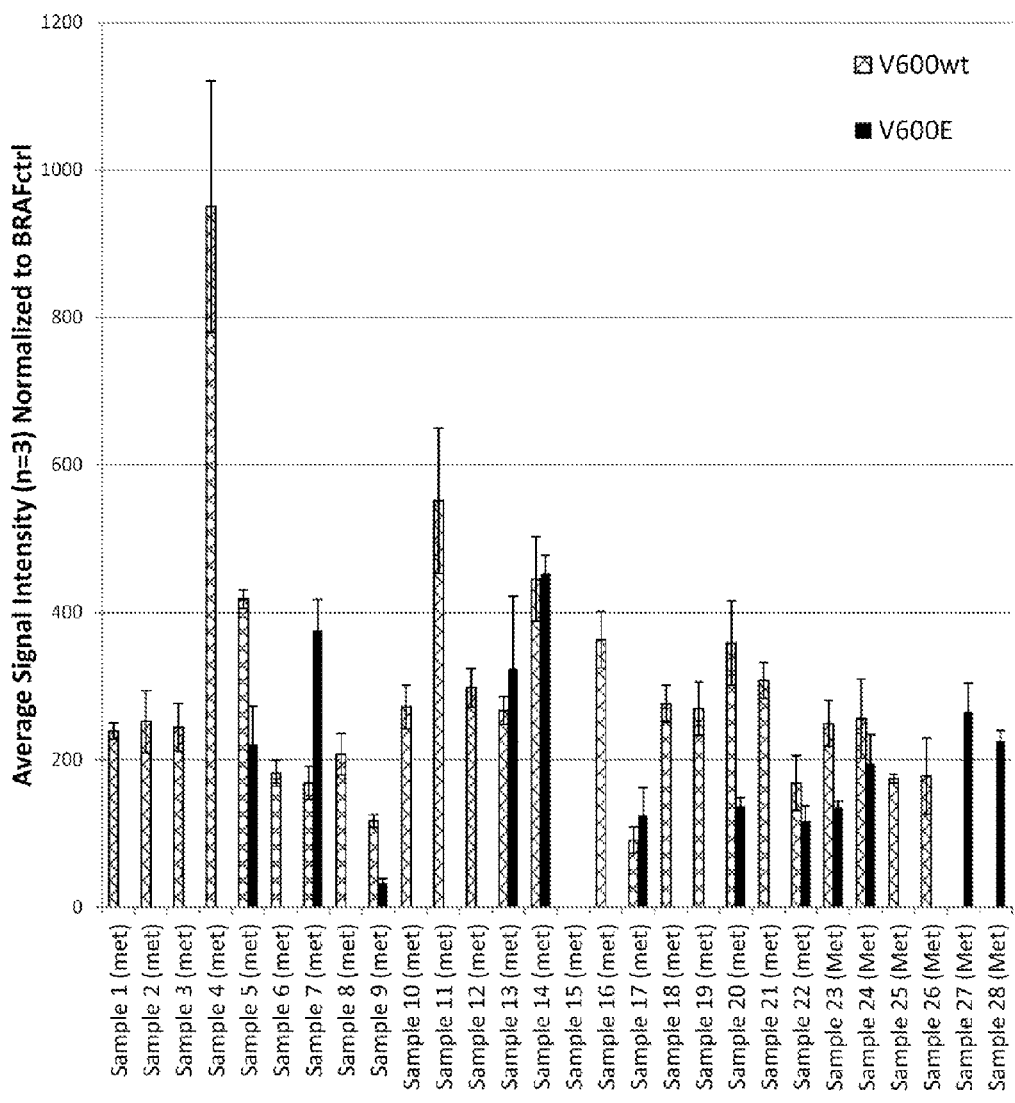
FIGS. 8A and B are a pair of graphs showing average signal intensity of V600 wild type and V600E probes in FFPE samples from metastatic (met) or primary (pri) melanomas.
Figure 8B:
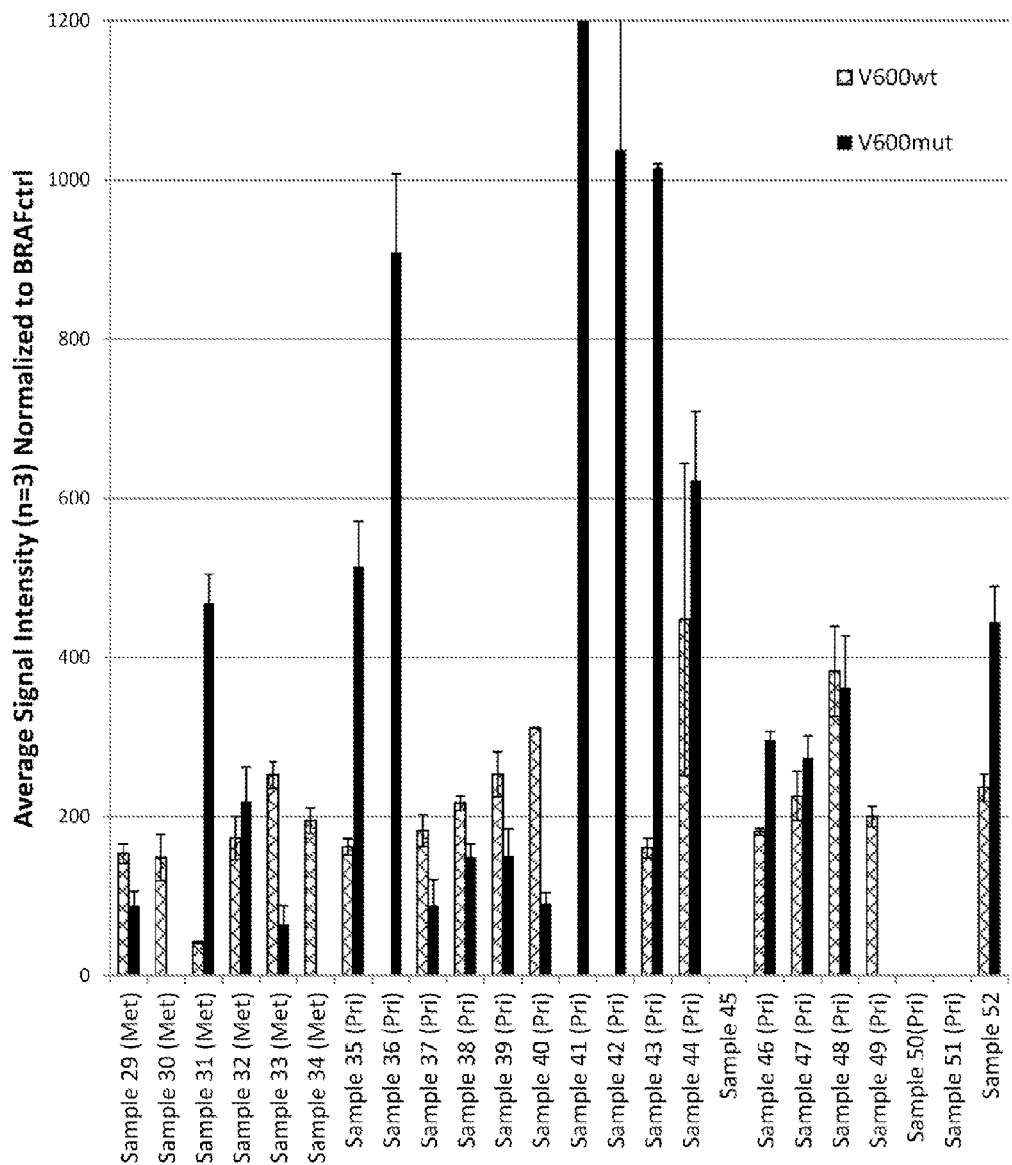

A series of 52 FFPE samples of primary or metastatic melanoma were tested for present of BRAF V600E mutation using the protocol described in Example 1, except that S1 nuclease reaction was carried out at 60° C. The FFPE samples were prepared using the protocol in Example 2. There was insufficient signal to make a call for 4 of the samples. The BRAF V600E mutation was identified in 26 of the 48 samples (54%) with sufficient signal (FIG. 8A-B). This is consistent with published frequency of BRAF mutations in melanoma (Davies et al., *Nature* 417:949-954, 2002).

In view of the many possible embodiments to which the principles of the disclosure may be applied, it should be recognized that the illustrated embodiments are only examples, and should not be taken as limiting the scope of the invention. Rather, the scope of the invention is defined by the following claims. I therefore claim as my invention all that comes within the scope and spirit of these claims.

We claim:

1. A method of detecting presence of a nucleotide variant in a target nucleic acid molecule in a sample, comprising:
contacting the sample with at least two probes complementary to the target nucleic acid molecule, wherein the target nucleic acid molecule comprises a nucleotide variant, under conditions sufficient for the first probe and the second probe to hybridize to the target nucleic acid, producing a mixture of hybridized nucleic acid molecules and unhybridized nucleic acid molecules,
wherein the first probe is complementary to wild type at the target nucleic acid molecule nucleotide variant, wherein the target nucleic acid molecule nucleotide variant position is two to six bases from a 3'-end of the first probe, and wherein the second probe is complementary to a first variant for the target nucleic acid molecule nucleotide variant, wherein the target nucleic acid nucleotide variant position is two to six bases from a 5'-end of the second probe, and wherein the first and the second probe overlap at the 3'-end of the first probe and the 5'-end of the second probe; or
wherein the first probe is complementary to wild type at the target nucleic acid molecule nucleotide variant, wherein the target nucleic acid molecule nucleotide variant position is two to six bases from a 5'-end of the first probe, wherein the second probe is complementary to a first variant for the target nucleic acid molecule nucleotide variant, wherein the target nucleic acid nucleotide variant position is two to six bases from a 3'-end of the second probe, and wherein the first and second probe overlap at the 5'-end of the first probe and the 3'-end of the second probe;
contacting the mixture of hybridized nucleic acid molecules and unhybridized nucleic acid molecules with a nuclease specific for single-stranded nucleic acid molecules under conditions sufficient to remove the unhybridized nucleic acid molecules; and
detecting presence of one or more of the probes in the mixture, thereby detecting presence of the nucleotide variant in the sample.

2. The method of claim 1, wherein the first probe and the second probe each comprise a detectable label.

3. The method of claim 2, wherein the first probe and the second probe are end-labeled.

4. The method of claim 3, wherein:
(i) the target nucleic acid molecule nucleotide variant position is two to six bases from the 5'-end of the first probe and the detectable label is at the 5'-end of the first probe, and
the target nucleic acid molecule nucleotide variant position is two to six bases from the 3'-end of the second probe and the detectable label is at the 3'-end of the second probe; or
(ii) the target nucleic acid molecule nucleotide variant position is two to six bases from the 3'-end of the first probe and the detectable label is at the 3'-end of the first probe, and
the target nucleic acid molecule nucleotide variant position is two to six bases from the 5'-end of the second probe and the detectable label is at the 5'-end of the second probe.

5. The method of claim 3, wherein the first probe and the second probe each comprise the detectable label at the 5'-end or wherein the first probe and the second probe each comprise the detectable label at the 3'-end.

6. The method of claim 2, wherein the detectable label comprises a hapten, a fluorescent molecule, an enzyme, or a radioisotope.

7. The method of claim 2, wherein detecting presence of one or more of the probes in the mixture comprises capillary electrophoresis.

8. The method of claim 2, wherein detecting presence of one or more of the probes in the mixture comprises:
contacting the mixture with a surface comprising multiple spatially discrete regions, each region comprising at least one anchor in association with a bifunctional linker comprising a first portion which specifically binds to the anchor and a second portion which specifically binds to one of the probes, under conditions sufficient for the probes to specifically bind to the second portion of the bifunctional linker; and
detecting presence of the detectable label.

9. The method of claim 2, wherein detecting presence of one or more of the probes in the mixture comprises:
contacting the mixture with a population of surfaces comprising a subpopulation of surfaces, wherein each subpopulation of surfaces comprises at least one anchor in association with a bifunctional linker comprising a first portion which specifically binds to the anchor and a second portion which specifically binds to one of the probes, under conditions sufficient for the probes to specifically bind to the second portion of the bifunctional linker; and
detecting presence of the detectable label.

10. The method of claim 9, wherein the population of surfaces comprises:
a first surface comprising substantially similar first anchors stably attached to the first surface and a second surface comprising substantially similar second anchors attached to the second surface, wherein the first anchors and second anchors are substantially different from each other;
a first bifunctional linker that has a first portion complementary to the first anchor and a second portion complementary to the first probe; and
a second bifunctional linker that has a first portion complementary to the second anchor and a second portion complementary to the second probe.

11. The method of claim 1, wherein the conditions sufficient for the at least two probes to hybridize to the target nucleic acid molecule comprise incubating the at least two probes with the sample at about 50° C. for about 16 hours.

12. The method of claim 1, wherein the at least two probes each comprise 18 to 75 nucleotides.

13. The method of claim 1, wherein at least one of the probes comprises one or more modified nucleotides.

14. The method of claim 13, wherein the one or more modified nucleotides comprises a locked nucleic acid, a peptide nucleic acid, an unnatural nucleotide, or a combination of two or more thereof.

15. The method of claim 1, wherein the nuclease specific for single-stranded nucleic acid molecules comprises S1 nuclease.

16. The method of claim 1, wherein detecting presence of one or more of the probes in the mixture comprises sequencing, nucleic acid amplification, or mass spectrometry.

17. The method of claim 1, further comprising lysing the sample.

18. The method of claim 1, wherein the sample comprises, tissue, fixed tissue, a tumor biopsy, cells, blood, a bodily fluid, or isolated nucleic acid.

19. The method of claim 18, wherein the isolated nucleic acid comprises RNA or mRNA.

20. A method of detecting presence of a nucleotide variant in a target nucleic acid molecule in a sample, comprising:

contacting the sample with at least two probes complementary to the target nucleic acid molecule, wherein the target nucleic acid molecule comprises a nucleotide variant, under conditions sufficient for the first probe and the second probe to hybridize to the target nucleic acid, producing a mixture of hybridized nucleic acid molecules and unhybridized nucleic acid molecules, wherein the first probe is complementary to wild type at the target nucleic acid molecule nucleotide variant, wherein the target nucleic acid molecule nucleotide variant position is at least two bases from a 3'-end of the first probe, and wherein the second probe is complementary to a first variant for the target nucleic acid molecule nucleotide variant, wherein the target nucleic acid nucleotide variant position is at least two bases from a 5'-end of the second probe, wherein the first probe comprises a detectable label at the 3'-end of the first probe, wherein the second probe comprises a detectable label at the 5'-end of the second probe, and wherein the first and the second probe overlap at the 3'-end of the first probe and the 5'-end of the second probe; or wherein the first probe is complementary to wild type at the target nucleic acid molecule nucleotide variant, wherein the target nucleic acid molecule nucleotide variant position is at least two bases from a 5'-end of the first probe, wherein the second probe is complementary to a first variant for the target nucleic acid molecule nucleotide variant, wherein the target nucleic acid nucleotide variant position is at least two bases from a 3'-end of the second probe, wherein the first probe comprises a detectable label at the 5'-end of the first probe, wherein the second probe comprises a detectable label at the 3'-end of the second probe, and wherein the first and the second probe overlap at the 5'-end of the first probe and the 3'-end of the second probe;

contacting the mixture of hybridized nucleic acid molecules and unhybridized nucleic acid molecules with a nuclease specific for single-stranded nucleic acid molecules under conditions sufficient to remove the unhybridized nucleic acid molecules; and detecting presence of one or more of the probes in the mixture, thereby detecting presence of the nucleotide variant in the sample.

* * * * *

SEQUENCE LISTING

```
<160> NUMBER OF SEQ ID NOS: 16

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide probe

<400> SEQUENCE: 1
tggtccctca ttgcactgta ctcctcttg                                    29

<210> SEQ ID NO 2
<211> LENGTH: 29
<212> TYPE: DNA
<213> ORGANISM: Artificial Sequence
<220> FEATURE:
<223> OTHER INFORMATION: Synthetic oligonucleotide probe

<400> SEQUENCE: 2
tcgtgacctg ctgtgtcgag aatatccaa                                    29

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 3
```

```
gctggccatc acgtaggctt catcga                                          26

<210> SEQ ID NO 4
<211> LENGTH: 33
<212> TYPE: DNA
<213> ORGANISM: Artificial Sequence
<220> FEATURE:
<223> OTHER INFORMATION: Synthetic oligonucleotide probe

<400> SEQUENCE: 4
atagaggatt tccttgttgg ctttcggaga tgt                                  33

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 5
agccgaaggg catgagctgc gtg                                             23

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 6
gcatgatgag ctgcacggtg gaggt                                           25

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 7
ccgcacccag cagtttggcc agc                                             23

<210> SEQ ID NO 8
<211> LENGTH: 29
<212> TYPE: DNA
<213> ORGANISM: Artificial Sequence
<220> FEATURE:
<223> OTHER INFORMATION: Synthetic oligonucleotide probe

<400> SEQUENCE: 8
cccgcccaaa atctgtgatc ttgacatgc                                       29

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 9
caaggcactc ttgcctacgc cacca                                           25

<210> SEQ ID NO 10
<211> LENGTH: 36
<212> TYPE: DNA
<213> ORGANISM: Artificial Sequence
```

```
<220> FEATURE:
<223> OTHER INFORMATION: Synthetic oligonucleotide probe

<400> SEQUENCE: 10
catcagctcc aactaccaca agtttatatt cagtca                                36

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 11
gtgcgtcgag tacgggaagc cga                                              23

<210> SEQ ID NO 12
<211> LENGTH: 43
<212> TYPE: DNA
<213> ORGANISM: Homo sapiens

<400> SEQUENCE: 12
acctccaccg tgcagctcat cacgcagctc atgcccttcg gct                        43

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 13
tggaggtggc acgtcgagta gtacg                                            25

<210> SEQ ID NO 14
<211> LENGTH: 43
<212> TYPE: DNA
<213> ORGANISM: Homo sapiens

<400> SEQUENCE: 14
acctccaccg tgcagctcat catgcagctc atgcccttcg gct                        43

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide probe

<400> SEQUENCE: 15
gatgggaccc actccatcga gatttcactg                                       30

<210> SEQ ID NO 16
<211> LENGTH: 41
<212> TYPE: DNA
<213> ORGANISM: Artificial Sequence
<220> FEATURE:
<223> OTHER INFORMATION: Synthetic oligonucleotide probe

<400> SEQUENCE: 16
ttctctgtag ctagaccaaa atcacctatt tttactgtga g                          41
```